United States Patent [19]
Allen et al.

[11] Patent Number: 5,917,057
[45] Date of Patent: Jun. 29, 1999

[54] N-HYDROXY-DIBENZ[B,E] OXEPINALKYLAMINES, N-HYDROXY-DIBENZ[B,E]OXEPINALKANOIC ACID AMIDES AND RELATED HETEROCYCLIC ANALOGUES

[75] Inventors: Richard C. Allen, Flemington; Grover C. Helsley, Stockton; R. Richard L. Hamer, Lebanon; Brian S. Freed, Somerset, all of N.J.; John I. White, Chapel Hill, N.C.; Lawrence L. Martin, Lebanon, N.J.

[73] Assignee: Hoechst Marion Roussel, Inc., Bridgewater, N.J.

[21] Appl. No.: 09/032,240

[22] Filed: Feb. 27, 1998

Related U.S. Application Data

[62] Division of application No. 08/207,464, Mar. 8, 1994, Pat. No. 5,840,749, which is a continuation of application No. 07/936,494, Aug. 28, 1992, abandoned, which is a continuation-in-part of application No. 07/651,850, Feb. 7, 1991, abandoned, which is a continuation-in-part of application No. 07/398,607, Aug. 25, 1989, abandoned.

[51] Int. Cl.$^6$ ............ C07D 333/74; C07D 313/00; A61K 31/38; A61K 31/335
[52] U.S. Cl. ............ 549/48; 549/354; 514/443; 514/450
[58] Field of Search ............ 549/48, 354; 514/443, 514/450

[56] References Cited

U.S. PATENT DOCUMENTS

| | | | |
|---|---|---|---|
| 4,477,465 | 10/1984 | Martin et al. | 424/275 |
| 4,496,580 | 1/1985 | Martin et al. | 514/443 |
| 4,514,411 | 4/1985 | Martin et al. | 514/215 |
| 4,515,946 | 5/1985 | Martin et al. | 548/237 |
| 4,526,891 | 7/1985 | Martin et al. | 514/253 |
| 4,585,788 | 4/1986 | Helsley et al. | 514/450 |
| 4,943,587 | 7/1990 | Cetenko et al. | 514/415 |
| 4,981,865 | 1/1991 | Belliotti et al. | 514/480 |
| 5,075,330 | 12/1991 | Belliotti et al. | 514/450 |
| 5,726,325 | 3/1998 | Yoshida et al. | 549/48 |
| 5,780,501 | 7/1998 | Betschart et al. | 514/450 |

FOREIGN PATENT DOCUMENTS 0235796  9/1987  European Pat. Off.

OTHER PUBLICATIONS

Aultz, et al., Dibenz[b,e]oxepin–alkanoic Acids as Nonsteroidal Antiinflammatory Agents, J. Med. Chem., vol. 20, No. 3, 456–58 (1977).

Aultz, et al., Dibenz[b,e]oxepin–alkanoic Acids as Nonsteroidal Antiinflammatory Agents, J. Med. Chem., vol. 20, No. 1, 66–70 (1977).

Aultz, et al., Dibenz[b,e]oxepin–alkanoic Acids as Nonsteroidal Antiinflammatory Agents, J. Med. Chem., vol. 20, No. 11, 1499–1501 (1977).

Yoshioka, et al., Nonsterooidal Antiinflammatory Agents, J. Med. Chem., vol. 21, No. 7, 633–639 (1978).

Summers, et al., Hydoxamic Acid Inhibitors of 5–Lipoxygenase, J. Med. Chem., vol. 30, No. 3, 574–580 (1987).

*Primary Examiner*—Deborah C. Lambkin
*Attorney, Agent, or Firm*—Edlyn S. Simmons; Barbara V. Maurer

[57] ABSTRACT

This invention relates to N-hydroxy-dibenz[b,e]oxepinalkylamines, N-hydroxy-dibenz[b,e]oxepinalkanoic acid amides and related heterocyclic analogues of the formula

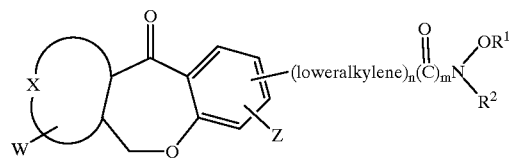

where X together with the carbon atoms to which it is attached forms a benzene or thiophene ring; W and Z are independently hydrogen, halogen, loweralkyl, or trifluoromethyl; $R^1$ is hydrogen, arylloweralkyl, loweralkoxycarbonyl, loweralkylcarbonyl, arylcarbonyl or arylloweralkylcarbonyl; $R^2$ is loweralkyl, cycloalkyl, arylloweralkyl, loweralkoxycarbonyl, loweralkylcarbonyl, arylcarbonyl or arylloweralkylcarbonyl; m is 0 or 1 and n is an integer of 0 to 4 or the pharmaceutically acceptable salts thereof. The compounds of this invention are useful as analgesics and topical antiinflammatory agents for the treatment of various dermatoses and agents for the treatment of conditions where accumulation of cyclooxygenase and/or lipoxygenase metabolites is a causative factor.

30 Claims, No Drawings

N-HYDROXY-DIBENZ[B,E] OXEPINALKYLAMINES, N-HYDROXY-DIBENZ[B,E]OXEPINALKANOIC ACID AMIDES AND RELATED HETEROCYCLIC ANALOGUES

This applications is a division of U.S. patent application Ser. No. 08/207,464, filed Mar. 8, 1994, U.S. Pat. No. 5,840,749, which is a continuation of U.S. patent application Ser. No. 07/936,494, filed Aug. 28, 1992, now abandoned, which is a continuation-in-part application of U.S. patent application Ser. No. 07/651,850, filed Feb. 7, 1991 now abandoned, which is a continuation-in-part application of patent application Ser. No. 07/398,607 filed Aug. 25, 1989, which is now abandoned.

This invention relates to compounds of the formula

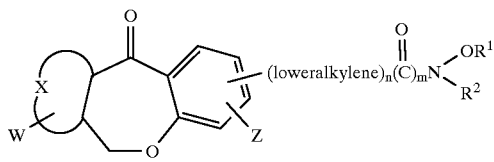

(I)

where X together with the carbon atoms to which it is attached forms a benzene or thiophene ring; W and Z are independently hydrogen, halogen, loweralkyl or trifluoromethyl; $R^1$ is hydrogen, arylloweralkyl, loweralkoxycarbonyl, loweralkylcarbonyl, arylcarbonyl or arylloweralkylcarbonyl; $R^2$ is loweralkyl, cycloalkyl, loweralkoxycarbonyl, arylloweralkyl, loweralkylcarbonyl, arylcarbonyl or aryl-loweralkylcarbonyl; m is 0 or 1 and n is an integer of 0 to 4 or the pharmaceutically acceptable salts thereof, or where applicable an optical, geometrical or stereoisomer or racemic mixture thereof. These compounds are useful as analgesics and as topical antiinflammatory agents for the treatment of ocular inflammation and various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis). Additionally, these compounds are useful as inhibitors of cyclooxygenase and/or lipoxygenase pathways and thus useful for alleviating inflammation, such as that associated with arthritis, inflammation of the gastrointestinal tract, allergy and asthma, and other conditions in which cyclooxygenase and/or lipoxygenase products are a causative factor.

Preferred embodiments of the invention are those substituents of Formula I wherein X together with the carbon atoms to which it is attached forms a benzene or thiophene ring; $R^1$ is selected from hydrogen, loweralkoxycarbonyl, loweralkylcarbonyl, arylcarbonyl or arylloweralkylcarbonyl; and $R^2$ is loweralkyl, cycloalkyl or loweralkylcarbonyl.

This invention also relates to compounds of the formula

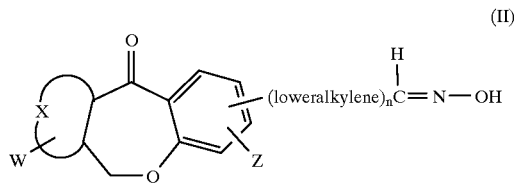

(II)

where W, X, Z and n are as previously defined.

Additionally, this invention relates to compounds of the formula

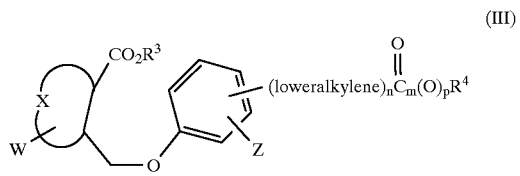

(III)

where W, X, Z, m and n are as previously defined and $R^3$ is hydrogen and loweralkyl, $R^4$ is hydrogen, hydroxy, loweralkyl and loweralkoxy; and p is 0 or 1. These compounds are useful as intermediates for the synthesis of compounds of Formula I.

Finally, this invention relates to compounds of the general formula

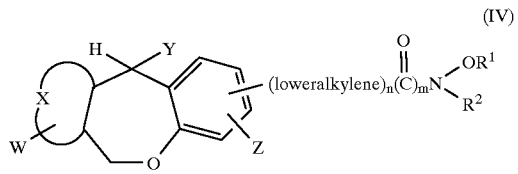

(IV)

where W, X, Z, m, n, $R^1$ and $R^2$ are as previously defined and Y is hydrogen or hydroxy. These compounds are also useful as analgesics and as topical antiinflammatory agents for the treatment of ocular inflammation and various dermatoses including, for example, exogenous dermatitides (e.g. sunburn, photoallergic dermatitis, urticaria, contact dermatitis, allergic dermatitis), endogenous dermatitides (e.g. atopic dermatitis, seborrheic dermatitis, nummular dermatitis), dermatitides of unknown etiology (e.g. generalized exfoliative dermatitis), and other cutaneous disorders with an inflammatory component (e.g. psoriasis). Additionally, these compounds are useful as inhibitors of cyclooxygenase and/or lipoxygenase pathways and thus useful for alleviating inflammation, such as that associated with arthritis, inflammation of the gastrointestinal tract, allergy and asthma, and other conditions in which cyclooxygenase and/or lipoxygenase products are a causative factor.

Throughout the specification and the appended claims, a given chemical formula or name shall encompass all optical, geometrical and stereoisomers thereof and racemic mixtures where such isomers and mixtures exist.

The term loweralkyl shall mean a straight or branched alkyl group having from 1 to 6 carbon atoms. Examples include methyl, ethyl, n-propyl, iso-propyl, n-butyl, iso-butyl, sec-butyl, t-butyl and straight and branched-chain pentyl and hexyl. The term cycloalkyl shall mean a cycloalkyl group of 3 to 7 carbon atoms.

The term halogen shall mean fluorine, chlorine, bromine or iodine.

The term aryl shall mean a phenyl group optionally substituted with one or more loweralkyl, loweralkoxy, halogen or trifluoromethyl groups.

The compounds of the present invention are prepared in the following manner. The substituents W, X, Y, Z, $R^1$, $R^2$, $R^3$, m and n are as defined above unless indicated otherwise.

Compound V of the formula

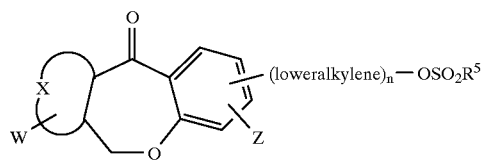

(V)

where $R^5$ is loweralkyl, is reacted with an N-loweralkylhydroxylamine hydrochloride or N-cycloalkylhydroxylamine hydrochloride, e.g., N-methylhydroxylamine hydrochloride, N-ethylhydroxyalamine hydrochloride, N-isopropylhydroxylamine hydrochloride or N-cyclohexylhydroxylamine hydrochloride, in the presence of a strong base, e.g., potassium t-butoxide or sodium methoxide, in a standard animation reaction to form Compound I of the invention, where m=0 and n is not equal to 0; that is, compound VI.

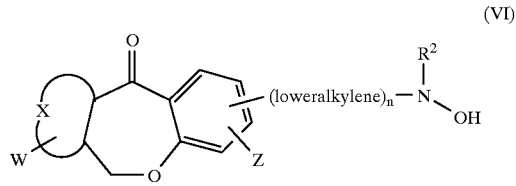

(VI)

This reaction is carried out under conventional animation reaction conditions, typically in the presence of a polar anhydrous solvent, e.g., methanol, ethanol, propanol or a suitable mixture of such solvents, at a temperature of 0° C. to reflux for 1 to 24 hours. Compound V where X is part of a benzene ring, can typically be prepared in the manner described in Martin et al., U.S. Pat. No. 4,526,891.

Compound V of the invention, where X is part of a thiophene ring, is prepared by the reaction of Compound VII of the formula

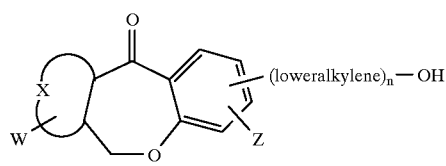

(VII)

with an alkylsulfonyl halide of the formula

$R^5SO_2Hal$ where $R^5$ is as previously defined and Hal is halogen. This reaction is carried out under standard conditions, typically in a polar basic solvent, e.g., pyridine, at a temperature of −10° C. to 25° C. for 1 to 24 hours. Compound VII can typically be prepared in the manner described in Martin et al., J. Med. Chem., 27, pp. 372–376 (1984).

The N-loweralkyl or N-cycloalkyl acid amides of the invention of the formula VIII (Compound I where m=1)

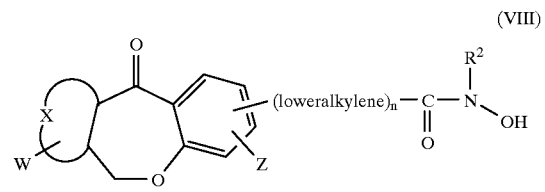

(VIII)

can be prepared in the following manner.

Compound IX of the formula

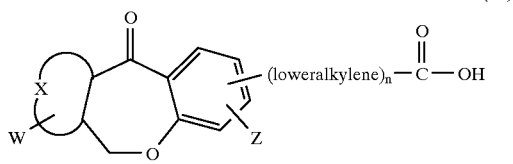

(IX)

is reacted with a halogenating agent, e.g., thionyl chloride or $POCl_3$, to afford Compound X of the formula

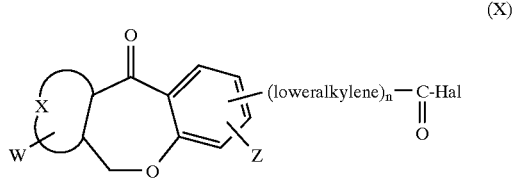

(X)

where Hal is halogen. This reaction is typically performed in the manner described in Martin et al., U.S. Pat. No. 4,515, 946. Compound IX is typically prepared in the manner described in Martin et al., J. Med. Chem., 27, pp. 372–376 (1984).

Compound X is reacted with an N-loweralkylhydroxylamine hydrochloride or N-cycloalkylhydroxylamine hydrochloride where loweralkyl and cycloalkyl are as previously defined, in the presence of a base, e.g., pyridine or 4-dimethylaminopyridine, to form Compound VIII. This reaction is typically carried out in an ethereal solvent, e.g., tetrahydrofuran, bis(2-methoxyethyl)ether or diethyl ether, at a temperature of from about −10 to 25° C. for 1 to 24 hours. Compound X, where X is part of a benzene ring, is typically prepared in the manner described in Martin et al., U.S. Pat. No. 4,515,946.

Compound XI of the invention of the formula

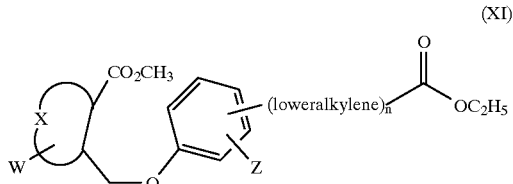

(XI)

an intermediate for the preparation of compound VIII is prepared by reacting Compound XII, a (hydroxyphenyl) alkanoic acid ethyl ester of the formula

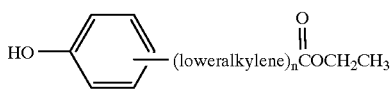

(XII)

with a 2-(halomethyl)benzoic acid methyl ester, compound XIII, of the formula

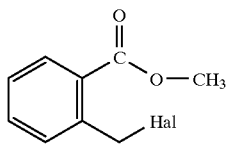

(XIII)

where Hal is halogen. This reaction is typically carried out in the presence of an acid acceptor, e.g., potassium carbonate, sodium carbonate or lithium carbonate, and a catalytic amount of a promoter, i.e., an alkali metal halide, e.g., sodium or potassium iodide. This reaction is carried out under conventional condensation reaction conditions, typically in the presence of a suitable solvent, e.g., 2-butanone or acetone at a temperature of about 25° C. to 80° C. to reflux for 1 to 48 hours.

Compound XI is typically hydrolyzed and cyclized using procedures described in Aultz et al., J. Med. Chem., 20, 1499–1501 (1977) or Martin et al., J. Med. Chem., 27, pp. 372–376 (1984) to form Compound IX.

Compound VII, an intermediate in the synthesis of Compound VI (Compound I where m=0) can be prepared in the following manner. Compound XIV,

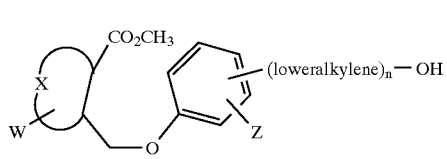

(XIV)

is prepared by reacting, Compound XV, an (hydroxyphenyl) alkanol of the formula

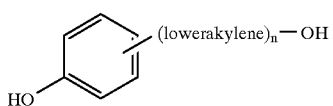

(XV)

with a 2-(halomethyl)benzoic acid methyl ester, (Compound XIII). This reaction is typically carried out in the presence of an acid acceptor, e.g., potassium carbonate, sodium carbonate or lithium carbonate, and a catalytic amount of a promoter, i.e., an alkali metal halide, e.g., potassium or sodium iodide. This reaction is carried out under conventional condensation reaction conditions, typically in the presence of a suitable solvent, e.g., 2-butanone or acetone, at a temperature of about 10° C. to 80° C. for 1 to 48 hours.

Compound XIV is hydrolyzed to afford Compound XVI of formula

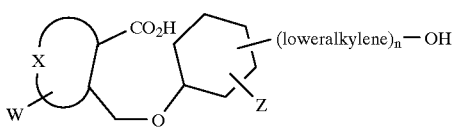

(XVI)

This hydrolysis is typically carried out with a base such as sodium or potassium hydroxide, in a suitable loweralkanol solvent, e.g., methanol, ethanol or propanol. This reaction typically takes place at a temperature of about 25° C. to 80° C. to reflux for 1 to 24 hours.

Typically, Compound XVI is cyclized by a method that will not interfere with the hydroxy group on the sidechain of the phenyl group, using trifluoroacetic acid anhydride, in an inert solvent, e.g., methylene chloride, as described in Martin et al., U.S. Pat. No. 4,496,580, to form Compound XVII of the formula

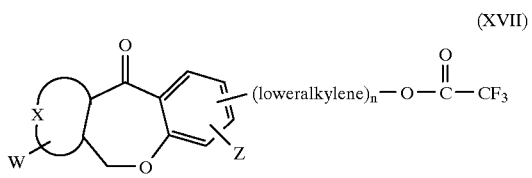

(XVII)

Acetylated Compound XVII is hydrolyzed under standard hydrolyzing conditions, e.g., in an aqueous solvent with a mineral acid, e.g., hydrochloric or sulfuric acid, at a temperature of about 50 to 80° C. to reflux for 4 to 24 hours followed by standard basification with a base, e.g., sodium bicarbonate, to form Compound VII.

Compound II of the invention is prepared by the reaction of Compound X with a reducing agent, e.g., lithium tri-tert-butoxyaluminohydride in an ethereal solvent, e.g., diglyme, at a temperature of about −80° C. to −70° C. for 1 to 2 hours to give intermediate XVIII of the formula

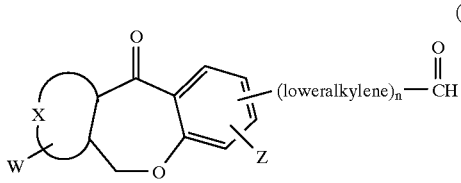

(XVIII)

Alternatively, Compound VII is reacted with an oxidizing agent, e.g., pyridinium chlorochromate in a halogenated solvent, e.g., dichloromethane, under nitrogen, at a temperature of about −20° C. to ambient temperature for 1 to 5 hours to form Compound XVIII. Compound XVIII where n=0 can be prepared from VII where n=2 via subsequent oxidation of XVIII where n=1 or it can be prepared in the manner described in Yoshioka et al., Journal of Med. Chem, 21, pp. 633–639 (1978).

Compound XVIII, an aldehyde, is reacted with pyridine and hydroxylamine hydrochloride to afford Compound II. This condensation reaction typically takes place in an anhydrous basic solvent, such as pyridine at ambient temperature to about 60° C. for 1 to 3 hours.

Compound XIX of the invention of the formula

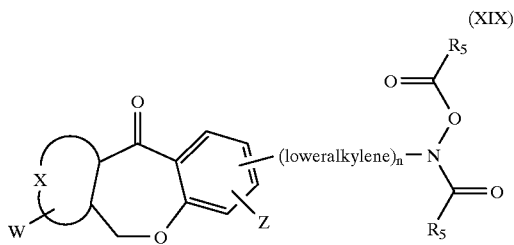

(XIX)

where $R^5$ is as previously defined, is prepared in the following manner.

Compound II, an aldoxime, is reacted with a reducing agent, e.g., borane, in a polar basic solvent, e.g., pyridine, at a temperature of about 0° C. to ambient temperature for 1 to 5 hours to afford Compound XX of the invention of the formula

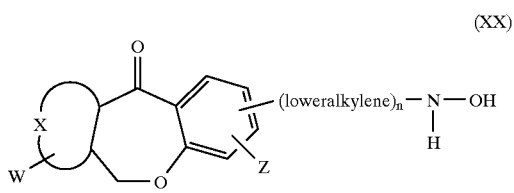

(XX)

Compound XX is reacted with a acylating agent, e.g., acetyl chloride, acetic anhydride or 2-methylpropionyl chloride, in a basic solvent, e.g., pyridine, to form Compound XIX of the invention. This reaction typically takes place under an inert gas, e.g., nitrogen, at a temperature of about −25° C. to ambient temperature for ½ to 5 hours.

Compounds of formula IV where Y is hydrogen are prepared in the following manner. Compound IX is reacted with a reducing agent under standard conditions to afford Compound XXI of the formula

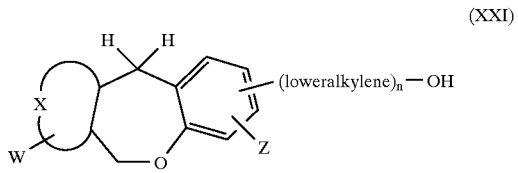

(XXI)

The reaction typically takes place in the presence of a reducing agent, e.g. borane, lithium aluminum hydride and the like, under a blanket of an inert gas such as nitrogen in an anhydrous ethereal solvent, e.g. tetrahydrofuran, bis(2-methoxyethyl)ether, diethyl ether or diisopropyl ether, at a temperature of from about −10 to 60° C.

Compound XXII of the formula

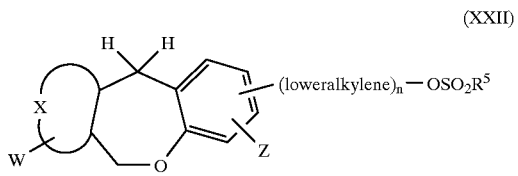

(XXII)

where $R^5$ is as previously defined, can typically be prepared from Compound XXI in the manner described in Martin et al., U.S. Pat. No. 4,526,891. Compound XXII is reacted with an N-loweralkylhydroxylamine hydrochloride or N-cycloalkylhydroxylamine hydrochloride in the presence of a strong base, e.g., potassium t-butoxide, sodium methoxide or triethylamine, in a standard amination reaction to form Compound XXIII, where n is not equal to 0.

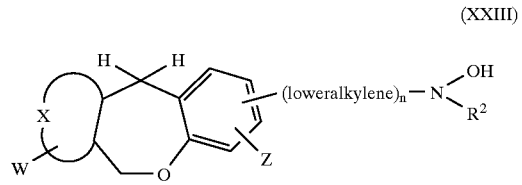

(XXIII)

The reaction is carried out under conventional amination reaction conditions, typically in the presence of a polar anhydrous solvent, e.g., methanol, ethanol, propanol or tetrahydrofuran or a suitable mixture of such solvents, at a temperature of 0° C. to reflux for 1 to 24 hours.

Alternatively, compound IX is reacted with a reducing agent such as zinc in acetic acid to give compound IXa. Compound IXa

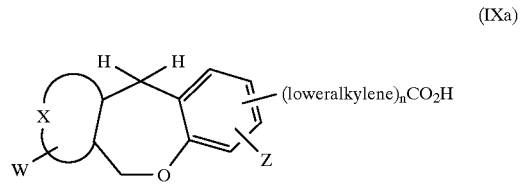

(IXa)

Compound IXa is subsequently reacted with oxalyl or thionyl chloride to yield compound Xa of the formula

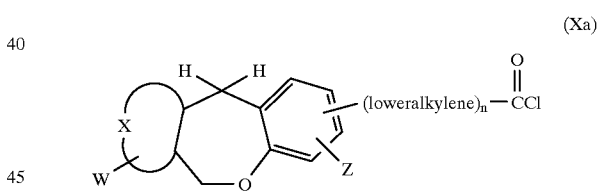

(Xa)

This reaction typically takes place in a solvent such as dichloromethane or dichloroethane at 0 to 50° C. for 2 to 24 hours. Compound Xa is reacted in a manner similar to that described above for Compound XXII to yield Compound XXIII.

Compound V is reacted with a compound of formula XXIV

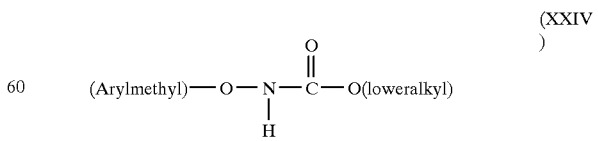

(XXIV)

in the presence of a strong base, e.g. sodium hydride, sodium methoxide or potassium t-butoxide, to form Compound XXV, where n is not equal to 0 and $R^6$ is loweralkoxy.

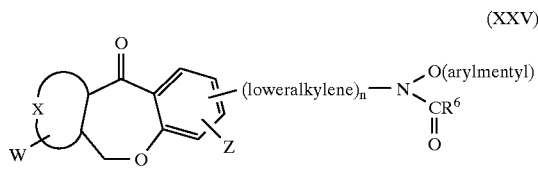

(XXV)

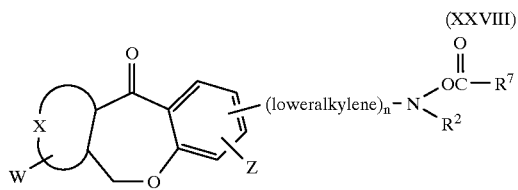

(XXVIII)

The reaction typically takes place under a blanket of an inert gas such as nitrogen, in an anhydrous polar solvent such as dimethylformamide, dimethylsulfoxide, tetrahydrofuran, methanol, ethanol or a suitable mixture of such solvents, at a temperature of 20 to 120° C for 1 to 48 hours. Compound XXIV is typically prepared in a similar manner to that so described by Sulsky, et al., Tetrahedron Letters, 30, pp. 31–34 (1989).

Compound XXVI of the formula

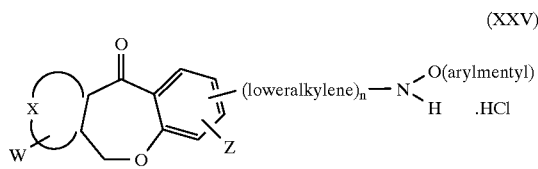

(XXV)

is typically prepared by reacting Compound XXV where $R^6$ is tertiary-butoxy with anhydrous hydrochloric acid in a polar solvent such as ethyl acetate or ethereal solvents, e.g., diethyl ether, bis(methoxyethyl)ether or tetrahydrofuran, or a suitable mixture of such solvents, at a temperature of 0 to 50° C. for 1 minute to 24 hours.

Compound XXVI is reacted with an acylating agent, e.g., acetyl chloride, acetic anhydride or 2-methylpropionyl chloride, in the presence of an acid acceptor, e.g. triethylamine, pyridine or potassium carbonate, to afford Compound XXV where $R^6$ is loweralkyl and n is not equal to 1. The reaction is typically carried out in a suitable solvent such as pyridine, chloroform, dichloromethane or tetrahydrofuran, at a temperature of about –25 to 25° C. for 30 minutes to 5 hours.

Compound XXVII of the formula

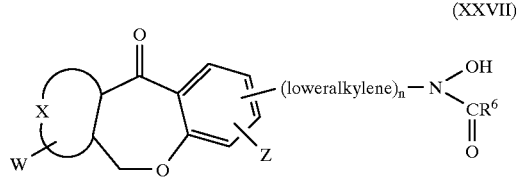

(XXVII)

is prepared by hydrogenolysis of Compound XXV. The reaction typically takes place in the presence of a catalyst such as palladium-on-carbon, in the presence of a hydrogen donor such as ammonium formate in a polar solvent such as ethanol or methanol, at about 0 to 50° C. for 1 to 8 hours.

Compound XXVIII of the formula where $R^7$ is loweralkyl or loweralkoxy is prepared by reacting Compound VI with an acylating agent, e.g., acetyl chloride, acetic anhydride, 2-methylpropionyl chloride, ethyl chloroformate, methyl chloroformate or di-t-butyl dicarbonate, in the presence of an acid acceptor, e.g. triethylamine, pyridine or potassium carbonate, to afford Compound XXV where $R^6$ is loweralkyl and n is not equal to 1. The reaction is typically carried out in a suitable solvent such as chloroform, dichloromethane or tetrahydrofuran, at a temperature of about –25 to 25° C. for 30 minutes to 5 hours.

To prepare compounds of formula IV where Y is OH, Compound I of the formula

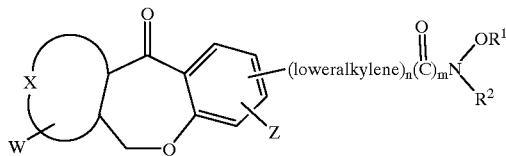

is reduced under standard conditions to afford Compound XXIX of the formula

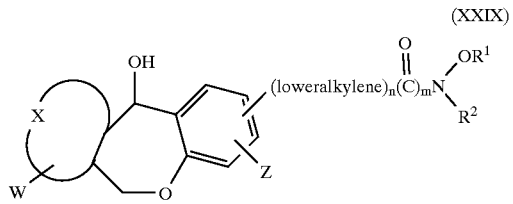

(XXIX)

This reaction typically takes place in the presence of a reducing agent such as sodium borohydride, lithium borohydride or calcium borohydride under a blanket of an inert gas such as nitrogen in a suitable solvent such as methanol, ethanol, isopropanol or tetrahydrofuran at a temperature of about –30 to 80° C.

Compounds of the present invention are useful as topical antiinflamatory agents for the treatment of various dermatoses which may include, for example, exogenous dermatitides (e.g., sunburn, photoallergic dermatitis, urticaria, contact dermatitis, allergic dermatitis), endogenous dermatitis (e.g., atopic dermatitis, seborrheic dermatitis, nummular dermatitis), dermatitides of unknown etiology (e.g., generalized exfoliative dermatitis), and other cutaneous disorders with an inflammatory component (e.g., psoriasis).

The dermatological activities of the compounds were ascertained according to the following methods.

DERMATOLOGICAL TEST METHODS

Phospholipase $A_2$-Induced Paw Edema (PIPE)

The ability of compounds to reverse naja naja (snake venom) phospholipase $A_2$(PLA$_2$)-induced paw edema in male Wistar rats (100–125 gm) was measured. PLA$_2$ (3 units/100 µl dH$_2$O/paw) alone or with 0.1 M of the test compound was injected in the subplantar region of the rat left hindpaw. Immediately following injection and at two hours post administration, the paw was immersed in a mercury bath, and paw displacement was measured on a recorder via a transducer. The value was then converted to mm Hg. (Standards: Quinacrine ED$_{50}$=0.1M; Hydrocortisone ED$_{50}$=0.46 M). Giessler, A. J. et al., "Agents and Actions", Vol. 10, "Trends in Inflammation Research" (1981), p. 195.

Arachidonic Acid-Induced Mouse Ear Edema (AAEE)

The purpose of this assay was to determine the ability of a topically applied compound to prevent mouse ear edema induced by topical application of arachidonic acid. Female Swiss Webster mice topically received vehicle or test compound (1.0 mg/ear) on both ears (10 µl on outer and inner ears). After 30 minutes, arachidonic acid is applied to the right ear of each mouse of each group in the amount of 4 mg/ear. Vehicle is applied to the left ear of each mouse of each group at a volume of 20 µl/ear. After an additional hour, the mice are sacrificed and a 4 mm plug is taken from each ear and weighed. The difference between the right and left ear plugs was determined for each animal. The antiinflammatory activity of the test compound is expressed as the mean percent change in the ear plug weight of the treated animals relative to the mean percent change in weights of control animals' ear. (Standard: Indomethacin—90% at 1 mg/ear). Young, J. M. et al., Invest. Dermatol., 80, (1983), pp. 48–52.

TPA-Induced Ear Edema (TPAEE)

The purpose of this assay was to determine the ability of a topically applied compound to prevent ear edema induced by topical application of TPA (phorbol 12-myristate acetate). Female Swiss Webster mice topically received TPA (10 µg/ear) on the right ear and vehicle on the left ear. The test compound (10 µg/ear) was applied to both ears. After about 5 hours, the animals are sacrificed and a 4 mm diameter plug is taken from each ear and weighed. The difference between the right and left ear plug weights for each animal was determined. The antiinflammatory activity of the test compound is expressed as the mean percent change in ear plug weight of the treated animals compared to the mean percent change in the plug weight of the control animals. (Standard: Indomethacin:—86% at 1 mg/ear). Young, J. M. et al., J. Invest. Dermatol., 80 (1983), pp. 48–52.

Dermatological activities for some of the compounds of this invention are presented in Table 1.

TABLE 1

| Compound | PIPE 0.1M | AAEE % Change @ 1 mg/ear | TPAEE 10 µg/ear |
|---|---|---|---|
| 2-(6,11-dihydro-11-oxodi-benz[b,e]oxepin-2-yl)-N-hydroxy-N-methyl-ethylamine | −70 | −46 | −50 |
| 3-(6,11-dihydro-11-oxodi-benz[b,e]oxepin-2-yl)-N-hydroxy-N-methyl-propanamide | −46 | −63 | −71 |
| N-cyclohexyl-2-(6,11-dihydro-11-oxodibenz[b,e]oxepin-2-yl)-N-hydroxyacetamide | −85 | −29 | −52 |
| 2-(6,11-dihydrodibenz[b,e]-oxepin-2-yl)-N-ethyl-N-hydroxy-ethylamine | | −50 | −84 |
| 3-(6,11-dihydrodibenz[b,e]-oxepin-2-yl)-N-hydroxy-N-methyl-propanamide | | −67 | |

Inflammation reduction is achieved when the compounds of the invention are administered topically, including opthalmic administration, to a subject requiring such treatment as an effective topical dose of from 0.01 to 100 mg/kg of body weight per day. A preferred effective amount is about 10 to 50 mg/kg of body weight per day. It is to be understood however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The compounds of the present invention are also useful as analgesic agents due to their ability to alleviate pain in mammals. The activity of the compounds is demonstrated in the phenyl-para-benzoquinone writhing assay in mice, a standard assay for analgesia [Proc. Soc. Exptl. Biol. Med., 95, 729 (1957)].

The analgesic activity of some of the compounds expressed as either the subcutaneous dose at which 50% of the phenyl-para-quinone induced writhing is inhibited in the animals, i.e., the ED$_{50}$ value, or as the % decrease in writhing at a given dose is presented in Table 2.

TABLE 2

| Compound | ED$_{50}$ or % Inhibition of Writhing |
|---|---|
| 2-(6,11-Dihydro-11-oxodibenz[b,e]-oxepin-2-yl)-N-ethyl-N-hydroxy-propanamide | ED$_{50}$ = 3.6 mg/kg |
| 3-(6,11-Dihydro-11-oxodibenz[b,e]-oxepin-2-yl)-N-cyclohexyl-N-hydroxypropanamide | 76% at 20 mg/kg |
| N-Cyclohexyl-2-(6,11-dihydro-11-oxodibenz[b,e]oxepin-2-yl)-N-hydroxyacetamide | 68% at 20 mg/kg |
| Propoxyphene | ED$_{50}$ = 3.9 mg/kg |

The analgesic relief of pain is achieved when the compounds of the invention are administered to a subject requiring such treatment at an effective oral, parentereal or intravenous dose of from 0.01 to 100 mg/kg of body weight per day. A preferred effective dose within this range is from about 10 to 50 mg/kg of body weight per day. A particularly preferred effective amount is about 30 mg/kg of body weight per day. It is to be understood, however, that for any particular subject, specific dosage regimens should be adjusted according to the individual need and the professional judgment of the person administering or supervising the administration of the compound. It is further to be understood that the dosages set forth herein are exemplary only and that they do not, to any extent, limit the scope or practice of the invention.

The compounds of the present invention are also useful as inhibitors of certain enzymes as demonstrated in the In Vitro 5-Lipoxygenase Assay (5-HETE) and In Vitro Cyclooxygenase Assay ($PGE_2$).

The ability of a compound to reduce 5-HETE production by cell-free 5-lipoxygenase enzyme obtained from rat basophilic leukemia (RBL-1) cells was measured by a modified procedure of Cochran et al. [Biochem. Biophys. Res. Commun., 161, 1327 (1989)]. RBL-1 cell-free supernatants were prepared by a modification of the method of Jakschik et al., [Prostaglandins, 25, 767 (1983)]. Cells ($1 \times 10^9$) were collected by centrifugation (22°) and washed at 40° C. with 50 mM phosphate buffer at $5 \times 10^7$ cells/ml. Cells were lysed on ice for 45 seconds with a Teckmar sonic disrupter. The homogenate was centrifuged (4° C) for 25 minutes and the supernatant (5 $\mu$g protein/$\mu$l) was decanted and stored at −80° C. A 1% dimethylsulfoxide (DMSO) vehicle (DMSO in deionized water) was utilized at various concentrations of the test compound. Duplicate reactions were run in 35mM buffer in the presence of 5 $\mu$M ATP, 50 $\mu$M $CaCl_2$ and 10 $\mu$M arachidonic acid at 37° C. The reaction was terminated with 10 $\mu$l 0.3 citrate buffer and diluted with BGGE buffer (0.01M phosphate, 0.1% bovine gamma globulin, pH 8.5) containing 114 $\mu$M BHT with ice bath cooling. 5-Hydroxyeicosatetraenoic acid (5-HETE) levels were quantitated by radioimmunoassay according to standard procedures.

The ability of a compound to reduce cyclooxygenase metabolite formation in cultured 3T3 mouse fibroblasts (CCL92-3T3) was measured by radioimmunoassay of prostaglandin $E_2$ ($PGE_2$) levels in the culture media. The 3T3 cells were maintained in complete Dulbecco's Modified Eagles Medium (DMEM) containing 10% calf serum, 2 mM L-glutamine and 5000 units/ml of penicillin/streptomycin. After seeding in 24 mm tissue culture dishes at $2 \times 10^{-4}$ cells/well, the cells were cultured for 24 hours. Media was removed by aspiration and replaced with DMEM (1 ml/well, 4 wells/treatment) containing test compound, which was previously dissolved in ethanol, or vehicle at various concentrations. The cells were then incubated for 24 hours and $PGE_2$ levels in the media were quantitated by radioimmunoassay according to established procedure (Lingren et al., FEBS Lett., 48, 22). The mean value from duplicate determinations was utilized to assess the % change from control values for each treatment group.

The activity of some of the compounds of the invention expressed as the In Vitro $IC_{50}$ is presented in Table 3.

TABLE 3

ENZYME INHIBITON

| Compound | In Vitro $IC_{50}$ ($\mu$M) | |
|---|---|---|
| | 5-HETE | $PGE_2$ |
| 2-(6,11-dihydro-11-oxodibenz[b,e]oxepin-2-yl)-N-hydroxy-N-methyl-ethylamine | 0.24 | 0.1 |
| 3-(6,11-dihydro-11-oxodibenz[b,e]oxepin-2-yl)-N-hydroxy-N-methyl-propanamide | 0.05 | 0.78 |
| N-cyclohexyl-2-(6,11-dihydro-11-oxodibenz[b,e]oxepin-2-yl)-N-hydroxyacetamide | 0.50 | −17% @1 $\mu$M |
| 2-(6,11-dihydrodibenz[b,e]oxepin-2-yl-)N-ethyl-N-hydroxyethylamine | 0.28 | 0.46 |
| 3-(6,11-dihydrodibenz[b,e]oxepin-2-yl)-N-hydroxy-N-methylpropanamide | 0.08 | 1.00 |
| Ibuprofen (standard) | | .022 |
| BW-755c (standard) | 5.0 | |

The inhibition is achieved when the compounds of the invention are administered to a subject requiring such treatment at an effective topical, oral, parenteral or intravenous dose of from 0.01 to 100 mg/kg of body weight per day. A preferred effective dose within this range is from about 10 to 50 mg/kg of body weight per day. It is to be understood, however, that for any particular subject, specific dosage regimens should be adjusted according to the individual need and the professional judgment of the person administering or supervising the administration of the compound. It is to be further understood that the dosages set forth herein are exemplary only and that they do not to any extent limit the scope or practice of the invention.

Effective quantities of the compounds of the present invention may be administered to a patient by any of the various methods, for example, orally as in capsules or tablets, topically as in ointments, solutions or salves, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Preferred pharmaceutically acceptable salts of the invention include those derived from inorganic acids such as hydrochloric, hydrobromic, sulfuric, nitric, phosphoric and perchloric acids and the like, as well as organic acids such as tartaric, citric, acetic, succinic, maleic, fumaric and oxalic acids. Preferred pharmaceutically acceptable base addition salts include salts of alkali metals, e.g. sodium or potassium; alkaline earth metals, e.g. calcium or magnesium; or complex salts such as ammonium or substituted ammonium salts such as mono-, di- or trialkylammonium salts or mono-, di- or trihydroxyalkylammonium salts.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of the compounds of the invention, the active ingredient, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of the compounds of the invention.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel®, corn starch and the like; a lubricant such as magnesium strearate or Sterotex®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

For the purpose of topical administration, the active compounds of the invention may be incorporated into a solution, suspension, ointment, cream, gel, aerosol or salve. These preparations should contain at least 0.1% of active compound but may be varied to be between 0.05 and about 20% of the weight thereof. The amount of active compound in such compositions is such that a suitable dosage will be obtained. Preferred topically administered preparations should contain between 0.1 and 10% of active compound.

The topical compositions may also include the following components: water, fixed oils, polyethylene glycols, glycerol, petroleum stearic acid, beeswax, other synthetic solvents or mixtures thereof; antibacterial agents such as benzyl alcohol or methyl paraben; antioxidants such as α-tocopherol acetate; chelating agents such as ethylenediaminetetraacetic acid (EDTA); buffers such as acetates, citrates or phosphates; emulsifying agent such as polyoxyethylene monooleate and coloring materials and adjuvants such as ferric oxide or talc. The topical preparation can be enclosed in tubes, bottles or jars made of metal, glass or plastic.

Examples of the compounds of this invention include:

2-(6,11-Dihydro-11-oxodibenz[b,e]oxepin-2-yl)-N-hydroxy-N-methyl-ethylamine;

2-(6,11-Dihydro-11-oxodibenz[b,e]oxepin-2-yl)-N-hydroxy-N-methylacetamide;

2-(6,11-Dihydro-11-oxodibenz[b,e]oxepin-2-yl)-N-hydroxy-N-(1-methylethyl)acetamide;

2-(6,11-Dihydro-11-oxodibenz[b,e]oxepin-2-yl)-N-ethyl-N-hydroxyacetamide;

N-Cyclohexyl-2-(6,11-dihydro-11-oxodibenz[b,e]oxepin-2-yl)-N-hydroxyacetamide;

2-(6,11-Dihydro-11-oxodibenz[b,e]oxepin-2-yl)-N-ethyl-N-hydroxyethylamine;

2-(6,11-Dihydro-11-oxodibenz[b,e]oxepin-2-yl)-N-hydroxy-N-(2-methylethyl)ethylamine;

2-(6,11-Dihydro-11-oxodibenz[b,e]oxepin-2-yl)-N-hydroxy-N-(2-methylpropanamide;

4-[[2-(methoxycarbonyl)phenyl]methoxy]benzenepropionic acid ethyl ester;

2-(6,11-Dihydro-11-oxodibenz[b,e,]oxepin-2-yl)-N-ethyl-N-hydroxypropanamide;

3-(6,11-Dihydro-11-oxodibenz[b,e]oxepin-2-yl)-N-hydroxy-N-methylpropanamide;

3-(6,11-Dihydro-11-oxodibenz[b,e]oxepin-2-yl)propanyl chloride;

3-(6,11-Dihydro-11-oxodibenz[b,e]oxepin-2-yl)-N-hydroxy-N-(1-methylethyl)-propanamide;

3-(6,11-Dihydro-11-oxodibenz[b,e]oxepin-2-yl)-N-ethyl-N-hydroxypropanamide;

3-(6,11-Dihydro-11-oxodibenz[b,e]oxepin-2-yl)-N-cyclohexyl-N-hydroxypropanamide;

2-[[4-(3-Hydroxypropyl)phenoxy]methyl]benzoic acid;

2-[[4-(3-Hydroxypropyl)phenoxy]methyl]benzoic acid methyl ester;

3-(6,11-Dihydro-11-oxodibenz[b,e]oxepin-2-yl)propyl trifluoroacetate.

3-(6,11-Dihydro-11-oxodibenz[b,e]oxepin-2-yl)propanol;

3-(6,11-Dihydro-11-oxodibenz[b,e]oxepin-2-yl)-N-hydroxy-N-methyl-1-propylamine;

4-(4,10-Dihydro-10-oxothieno[3,2-c][1]benzoxepin-8-yl) butanol methanesulfonate;

4-(4,10-Dihydro-10-oxothieno[3,2-c][1]benzoxepin-8-yl)-N-hydroxy-N-methyl-1-butylamine;

N-[2-(6,11-Dihydro-11-oxodibenz[b,e]oxepin-2-yl)ethyl]-N-hydroxyacetylacetamide;

2-(6,11-Dihydro-11-oxodibenz[b,e]oxepin-2-yl) acetaldoxime;

N-[(6,11-Dihydro-11-oxodibenz[b,e]oxepin-2-yl)methyl]-N-hydroxyacetamide;

N-[2-(6,11-Dihydro-11-oxodibenz[b,e]oxepin-2-yl)ethyl]-N-hydroxy-1,1-dimethylethylcarbamate; mine;

N-[2-(6,11-Dihydro-11-oxodibenz[b,e]oxepin-2-yl)ethyl]-N-acetyloxyacetamide;

2-(6,11-Dihydro-11-oxodibenz[b,e]oxepin-2-yl)-N-ethyl-N-(ethoxycarbonyloxy)ethylamine;

2-(6,11-Dihydro-11-oxodibenz[b,e]oxepin-2-yl)-N-ethyl-N-(acetoxy)ethylamine;

2-(6,11-Dihydrodibenz[b,e]oxepin-2-yl)-N-ethyl-N-hydroxyethylamine;

2-Dihydro-11-hydroxydibenz[b,e]oxepin-2-yl)-N-ethyl-N-hydroxyethylamine;

2-(6,11-Dihydrodibenz[b,e]oxepin -2-yl)-N-methyl-N-hydroxyethylamine;

2-(6,11-Dihydro-11-hydroxydibenz[b,e]oxepin-2 -yl)-N-methyl-N-hydroxyethylamine;

N-[2-(6,11-Dihydrodibenz[b,e]oxepin-2-yl)ethyl]-N-hydroxyacetamide;

N-[(6,11-Dihydrodibenz[b,e]oxepin-2-yl)methyl]-N-hydroxyacetamide;

N-[2-(6,11-Dihydro-11-hydroxydibenz[b,e]oxepin-2-yl) ethyl]-N-hydroxyacetamide;

N-[(6,11-Dihydro-11-hydroxydibenz[b,e]oxepin-2-yl) methyl]-N-hydroxyacetamide;

3-(6,11-Dihydrodibenz[b,e]oxepin-2-yl)-N-methyl-N-hydroxypropanamide;

3-(6,11-Dihydro-11-hydroxydibenz[b,e]oxepin-2-yl)-N-methyl-N-hydroxypropanamide;

3-(6,11-Dihydrodibenz[b,e]oxepin-2-yl)-N-ethyl-N-hydroxypropanamide;

3-(6,11 -Dihydro-11-hydroxydibenz[b,e]oxepin-2-yl)-N-ethyl-N-hydroxypropanamide;

N-[2-(6,11-Dihydro-11-oxodibenz[b,e]oxepin-2-yl)ethyl]-N-phenylmethoxy-phenylmethoxy-1,1-dimethylethylcarbamate;

2-(6,11-Dihydro-11-oxodibenz[b,e]oxepin-2-yl)-N-(phenylmethoxy)ethylamine;

N-[2-(6,11-Dihydro-11-oxodibenz[b,e]oxepin-2-yl)ethyl]-N-(phenylmethoxy)acetamide;

2-(6,11-Dihydrodibenz[b,e]oxepin-2-yl)ethanol;
2-(6,11-Dihydrodibenz[b,e]oxepin-2-yl)ethanol methanesulfonate;
2-(4,10-Dihydrothienol[3,2c][1]benzoxepin-8-yl)-N-methyl-N-hydroxyethylamine;
2-(4,10-Dihydro-10-oxothieno[3,2c][1]benzoxepin-8-yl)-N-methyl-N-hydroxyethylamine;
2-(4,10-Dihydro-10-oxothieno[3,2c][1]benzoxepin-8-yl)-N-ethyl-N-hydroxyethylamine;
2-(4,10-Dihydrothieno[3,2c][1]benzoxepin-8-yl)-N-ethyl-N-hydroxyethylamine;
2-(4,10-Dihydro-10-oxo-thieno[3,2c][1]benzoxepin-8-yl)-N-hydroxy-N-methylpropanamide;
2-(4,10-Dihydrothieno[3,2c][1]benzoxepin-8-yl)-N-hydroxy-N-methylpropanamide;
3-(6,11-Dihydro-dibenz[b,e]oxepin-2-yl)propanoic acid;
3-(6,11-Dihydro-dibenz[b,e]oxepin-2-yl)-N-hydroxy-N-methylpropanamide; and
3-(6,11-Dihydro-11-oxodibenz[b,e]oxepin-2-yl)-2,2-dimethyl-N-hydroxy-N-methyl propanamide.

The following examples are for illustrative purposes and are not to be construed as limiting the invention disclosed herein. All temperatures are given in degrees centigrade.

EXAMPLE 1

2-(6,11-Dihydro-11-oxodibenz[b,e]oxepin-2-yl)-N-hydroxy-N-methyl-ethylamine

To a flask was added 25.08 g of potassium tert-butoxide and 18.68 g of N-methylhydroxylamine hydrochloride in 700 ml of 95% ethanol with stirring. To the mixture was added 15.02 g of finely ground 2-(6,11-dihydro-1 1 -oxodibenz[b,e]oxepin-2-yl)ethanol methanesulfonate and the stirred suspension was allowed to reflux for 24 hours. The suspension was concentrated to dryness and the solid residue was partitioned against 500 ml of 5% sodium bicarbonate and a total of 600 ml of methylene chloride. The dried (MgSO$_4$) organic phase was filtered and concentrated to an oil. Evaluation of the crude product (13.44 g) by thin layer analysis (silica gel, ethyl acetate) indicated a mixture, which was separated using preparative High Performance Liquid Chromatography (HPLC hereafter) (Waters Associates Prep LC/System 500, silica gel, ethyl acetate) to give 7.24 g of pure material. Recrystallization from methanol afforded 2-(6,11-dihydro-11-oxodibenz[b,e]oxepin-2-yl)-N-hydroxy-N-methyl-ethylamine, m.p. 101–102° C.

Analysis: Calculated for C$_{17}$H$_{17}$NO$_3$: 72.07%C 6.05%H 4.94%N; Found: 71.92%C 5.87%H 4.89%N

EXAMPLE 2

2-(6,11-Dihydro-11-oxodibenz[b,e]oxepin-2-yl)-N-hydroxy-N-methylacetamide

To a flask was added 11.6 g of N-methylhydroxylamine hydrochloride in 250 ml of pyridine. The mixture was stirred to afford a solution, and the flask was chilled with an ice bath. To the stirred solution was added, dropwise over several minutes, a solution of 10.0 g of 2-(6,11-dihydro-11-oxodibenz[b,e]oxepin-2-yl)acetyl chloride in 400 ml of tetrahydrofuran. After the addition was complete, the flask was allowed to equilibrate to room temperature with continued stirring for 24 hours. The suspension was condensed by half using rotary evaporation and was transferred to a separatory funnel. The mixture was partitioned against 300 ml of methylene chloride and 100 ml of 10% HCl (aqueous phase below pH 1). The dried (MgSO$_4$) organic phase was filtered and concentrated to an oil using rotary evaporation. Thin layer analysis indicated a mixture, which was separated via preparative HPLC to give 4.76 g of pure material. Recrystallization from acetone afforded 2-(6,11-dihydro-11-oxodibenz[b,e]oxepin-2-yl)-N-hydroxy-N-methylacetamide, m.p. 118–120° C.

Analysis: Calculated for C$_{17}$H$_{15}$NO$_4$: 68.68%C 5.09%H 4.71%N; Found: 68.77%C 5.06%H 4.68%N

EXAMPLE 3

2-(6,11-Dihydro-11-oxodibenz[b,e]oxepin-2-yl)-N-hydroxy-N-(1-methylethyl)acetamide To a flask was added 10.0 g of N-isopropylhydroxylamine hydrochloride in 400 ml of dry pyridine. The mixture was stirred to afford a solution, chilled with an ice bath and treated dropwise over several minutes with a solution of 5.72 g of 2-(6,11-dihydro-11-oxodibenz[b,e]oxepin-2-yl)acetyl chloride in 200 ml of dry tetrahydrofuran. The solution was stirred for 24 hours and was allowed to equilibrate to room temperature. The resulting cloudy suspension was condensed to an oil via rotary evaporation and was transferred to a separatory funnel. The product was partitioned against 500 ml of methylene chloride and a sufficient amount (500 ml) of 10% HCl to acidify the aqueous phase below pH 1. The dried (Na$_2$SO$_4$) organic phase was filtered and concentrated to an oil using rotary evaporation. Thin layer analysis indicated a mixture, which was separated via HPLC to give 3.92 g of pure material. Recrystallization from acetone afforded 2-(6,11-dihydro-11-oxodibenz[b,e]oxepin-2-yl)-N-hydroxy-N-(1-methylethyl)acetamide, m.p. 144–145° C.

Analysis: Calculated for C$_{19}$H$_{19}$NO$_4$: 70.14%C 5.89%H 4.30%N; Found: 70.14%C 5.88%H 4.24%N

EXAMPLE 4

2-(6,11-Dihydro-11-oxodibenz[b,e]oxepin-2-yl)-N-ethyl-N-hydroxyacetamide

To a flask was added 4.0 g of N-ethylhydroxylamine hydrochloride in 300 ml of dry pyridine. The mixture was stirred to afford a solution, chilled with an ice bath, and was treated dropwise over several minutes with a solution of 5.72 g of 2-(6,11-dihydro-11-oxodibenz[b,e]oxepin-2-yl)acetyl chloride in 200 ml of dry tetrahydrofuran. The solution was stirred for 24 hours while allowing the bath to equilibrate to room temperature. The resulting suspension was condensed to an oil via rotary evaporation and was then transferred to a separatory funnel. The product was partitioned against 500 ml of methylene chloride and a sufficient amount (250 ml) of 10% HCl to acidify the aqueous phase below pH 1. The organic phase was then washed with 250 ml of water. The dried (Na$_2$SO$_4$) organic phase was filtered and concentrated to an oil using rotary evaporation. Thin layer analysis indicated a mixture, which was separated via HPLC to give 3.03 g of pure material. The product was combined with another lot of identically prepared material, which was found to be pure by thin layer analysis. The total amount of combined material was 4.53 g. Recrystallization from acetone afforded 2-(6,11-dihydro-11-oxodibenz[b,e]-oxepin-2-yl)-N-ethyl-N-hydroxyacetamide, m.p. 119–121° C.

Analysis: Calculated for C$_{18}$H$_{17}$NO$_4$: 69.44%C 5.50%H 4.50%H Found: 69.63%C 5.45%H 4.29%N

EXAMPLE 5

N-Cyclohexyl-2-(6,11-dihydro-11-oxodibenz[b,e]oxepin-2-yl)-N-hydroxyacetamide

To a flask was added 4.0 g of N-cyclohexylhydroxylamine in 400 ml of dry pyridine. The mixture was stirred to afford a solution, chilled with an ice bath, and treated dropwise over several minutes with a solution of 4.86 g of 2-(6,11-dihydro-11-oxodibenz[b,e,]oxepin-2-yl)acetyl chloride in 200 ml of dry tetrahydrofuran. The solution was stirred for 24 hours, while allowing the bath to equilibrate to room temperature. The resulting solution was concentrated to an oil, via rotary evaporation, and was partitioned against 500 ml of methylene chloride and a sufficient amount (250 ml) of 10% HCl to acidify the aqueous phase below pH 1. The organic phase was then washed with 250 ml of distilled water. The dried ($Na_2SO_4$) organic phase was filtered and concentrated to an oil using rotary evaporation. Thin layer analysis indicated a mixture, which was separated via preparative HPLC to give 3.14 g of the product. Recrystallization from acetone afforded N-cyclohexyl-2-(6,11-dihydro-11-oxodibenz[b,e]oxepin-2-yl)-N-hydroxyacetamide, m.p. 130–131° C.

Analysis: Calculated for $C_{22}H_{23}NO_4$: 72.31%C 6.34%H 3.83%N; Found: 72.12%C 6.15%H 3.58%N

EXAMPLE 6

2-(6,11-Dihydro-11-oxodibenz[b,e]oxepin-2-yl)-N-ethyl-N-hydroxyethylamine

To a flask was added 4.48 g of potassium tert-butoxide and 3.95 g of N-ethylhydroxylamine hydrochloride in 500 ml of absolute ethanol. The suspension was stirred, and precipitation of potassium chloride was noted. To the suspension was added 3.32 g of finely ground 2-(6,11-dihydro-11-oxodibenz[b,e]oxepin-2-yl)ethanol methanesulfonate, and the slurry was allowed to reflux for 4½ hours. To the product mixture was added 500 ml of water and the solution was concentrated via rotary evaporation to remove ethanol. The resulting suspension was transferred to a separatory funnel and partitioned against a total of 600 ml of methylene chloride and 1000 ml of water. The dried ($Na_2SO_4$) organic phase was filtered and concentrated to an oil using rotary evaporation. Thin layer analysis indicated a mixture, which was separated via preparative HPLC to give 1.24 g of 2-(6,11-dihydro-11-oxodibenz[b,e]oxepin-2-yl)-N-ethyl-N-hydroxyethylamine m.p. 86–88° C.

Analysis: Calculated for $C_{18}H_{19}NO_3$: 72.71%C 6.44%H 4.71%N; Found: 72.45%C 6.40%H 4.57%N

EXAMPLE 7

2-(6,11-Dihydro-11-oxodibenz[b,e]oxepin-2-yl)-N-hydroxy-N-(2-methylethyl)ethylamine To a flask was added 14.37 g of potassium tert-butoxide and 13.08 g of N-isopropylhydroxylamine hydrochloride in 1500 ml of absolute ethanol. The suspension was stirred, and precipitation of potassium chloride was noted. To the suspension was added 10.62 g of finely ground 2-(6,11-dihydro-1-oxodibenz[b,e]oxepin-2-yl)ethanol methanesulfonate, and the slurry was allowed to reflux for 24 hours. To the product mixture was added 500 ml of water and the solution was concentrated via rotary evaporation to remove ethanol. The resulting suspension was transferred to a separatory funnel and partitioned against a total of 500 ml of methylene chloride and 1000 ml of water. The dried ($Na_2SO_4$) organic phase was filtered and concentrated to an oil using rotary evaporation. Thin layer analysis indicated a mixture, which was separated via preparative HPLC to give 3.20 g of pure material. Recrystallization from acetonitrile afforded 2-(6,11-dihydro-11-oxodibenz[b,e]oxepin-2-yl)-N-hydroxy-N-(2-methylethyl)ethylamine, m.p. 121–124° C.

Analysis: Calculated for $C_{19}H_{21}NO_3$: 73.29%C 6.80%H 4.50%N; Found: 73.55%C 6.52%H 4.67%N

EXAMPLE 8

2-(6,11-Dihydro-11-oxodibenz[b,e]oxepin-2-yl)-N-hydroxy-N-methylpropanamide

To a flask was added a solution of a few drops of dimethylformamide and 50.0 g of 2-(6,11-dihydro-11-oxodibenz[b,e,]oxepin-2-yl)propionic acid in methylene chloride, and the solution was chilled. To the cold solution was added dropwise over several minutes, 13.14 ml of thionyl chloride. The solution was intermittently warmed on a steam bath until all gas evolution ceased, and was allowed to stir for 24 hours. The solution was concentrated to an oil in vacuo to remove solvents and any unreacted thionyl chloride to give 45.4 g of the pure acid chloride.

A stirred solution of 16.6 g of N-methylhydroxylamine hydrochloride in 400 ml of dry pyridine was chilled and treated dropwise over several minutes with a solution of 15.7 g of 2-(6,11-dihydro11oxodibenz[b,e]oxepin-2-yl)propionyl chloride in 500 ml of tetrahydrofuran. The solution was allowed to equilibrate to room temperature with continued stirring. Thin layer analysis (silica gel, 30% hexane in ethyl acetate) indicated reaction completion after 5 hours. Pyridine and tetrahydrofuran were removed in vacuo and the resulting mixture was partitioned against a total of 700 ml of methylene chloride and 2000 ml of 10% HCl (pH of aqueous layers <1). The organic phase was washed with 500 ml of water. The dried ($Na_2SO_4$) organic phase was concentrated in vacuo to an oil. Thin layer analysis indicated a mixture, which was separated via preparative HPLC to give 10.58 g of the product, 2-(6,11-dihydro-11-oxodibenz[b,e]oxepin-2-yl)-N-hydroxy-N-methylpropanamide, as an oil.

Analysis: Calculated for $C_{18}H_{17}NO_4$: 69.44%C 5.50%H 4.50%N; 20 Found: 69.12%C 5.72%H 4.06%N

EXAMPLE 9

4-[[2-(methoxycarbonyl)phenyl]methoxy]benzenepropanoic acid ethyl ester

To a dry flask under inert atmosphere was added 97.0 g of 3-(4-hydroxyphenyl)propanoic acid, 207 g of potassium carbonate, and 1.0 g (cat.) of sodium iodide in 600 ml of 2-butanone. The suspension was rapidly purged using several vacuum/$N_2$ cycles. To the stirring suspension was added dropwise over 30 minutes, a solution of 114.5 g of 2-(bromomethyl)benzoic acid methyl ester in 1000 ml of 2-butanone. The resulting white suspension was allowed to reflux for 24 hours, cooled and allowed to stir at room temperature for 1 hour. The solids were removed by vacuum filtration and washed on the funnel. The solution was concentrated to an oil in vacuo. The oil was partitioned against a total of 500 ml of methylene chloride and 500 ml of 10% NaOH (pH of aqueous layers >11), and washed with 800 mL of water. The dried ($Na_2SO_4$) organic layer was concentrated to an oil in vacuo. Thin layer analysis indicated a mixture, which was separated via preparative HPLC to give 109.95 g of pure 4-[[2-(methoxycarbonyl)phenyl]methoxy]benzenepropionic acid ethyl ester as an oil.

Analysis: Calculated for $C_{20}H_{22}O_5$: 70.16%C 6.47%H; Found: 70.17%C 6.53%H

EXAMPLE 10

2-(6,11-Dihydro-11-oxodibenz[b,e]oxepin-2-yl)-N-ethyl-N-hydroxypropanamide

To a flask was added a solution of a few drops of dimethylformamide and 50.0 g of 2-(6,11-dihydro-11- oxodibenz[b,e,]oxepin-2-yl)propionic acid in 500 ml of methylene chloride, and the solution was chilled. To the chilled solution was added dropwise over several minutes, 13.14 ml of thionyl chloride. The solution was intermittently warmed on a steam bath until all gas evolution had ceased, and was then allowed to stir for 24 hours. The solution was concentrated to an oil in vacuo to remove solvents and any unreacted thionyl chloride to give 45.4 g of the pure acid chloride.

A stirring solution of 10.14 g of N-ethylhydroxylamine hydrochloride in 350 ml of dry pyridine was chilled and treated dropwise over several minutes with a solution of 8.0 g of 2-(6,11-dihydro-11-oxodibenz[b,e,]oxepin-2-yl) propionyl chloride in 400 ml of tetrahydrofuran. The solution was allowed to equilibrate to room temperature overnight (16 hours) with continued stirring. The reaction was quenched with 500 ml of water and concentrated in vacuo to remove solvents. The product mixture was partitioned against a total of 500 ml of methylene chloride and 1000 ml of 10% HCl (pH of aqueous layers <1). The organic phase was washed with 500 ml of water, dried ($Na_2SO_4$) and concentrated in vacuo to an oil. Thin layer analysis indicated a mixture, which was separated twice via preparative HPLC to give 2.65 g of 2-(6,11-dihydro-11-oxodibenz[b,e]-oxepin-2-yl)-N-ethyl-N-hydroxypropana as an oil.

Analysis: Calculated for $C_{19}H_{19}NO_4$: 70.14%C 5.89%H 4.30%N; Found: 69.64%C 6.02%H 4.11%N

EXAMPLE 11

3-(6,11-Dihydro-11-oxodibenz[b,e]oxepin-2-yl)-N-hydroxy-N-methylpropanamide

A stirring solution of 12.58 g of N-methylhydroxylamine hydrochloride in 300 ml of dry pyridine was chilled, degassed using several vacuum/$N_2$ cycles, and treated dropwise over several minutes with a solution of 9.06 g of 3-(6,11-dihydro-11-oxodibenz[b,e]oxepin-2-yl)propanyl chloride in 200 ml of dry tetrahydrofuran. The solution was allowed to equilibrate to room temperature overnight. The reaction was quenched with 200 ml of water, concentrated in vacuo to remove solvents, and partitioned against a total of 200 ml of methylene chloride and 200 ml of 10% hydrochloric acid (pH of the resulting aqueous phase was below 1). The organic phase was washed with 500 mL of water, dried ($Na_2SO_4$), and concentrated to an oil in vacuo. Thin layer analysis indicated mixture a which was separated via HPLC eluting with 50% methylene chloride in tetrahydrofuran to give 5.3 g of material. This material was again separated via HPLC under similar conditions using acetonitrile as eluant, to give 3.62 g of 3-(6,11-dihydro-11-oxodibenz[b,e]oxepin-2-yl)-N-hydroxy-N-methylpropanamide, as an oil.

Analysis: Calculated for $C_{18}H_{17}NO_4$: 69.44%C 5.50%H 4.50%N; Found: 69.24%C 5.62%H 4.50%N

EXAMPLE 12

3-(6,11-Dihydro-11-oxodibenz[b,e]oxepin-2-yl) propanyl chloride

To a flask was added a few drops of N,N-dimethylformamide and 35.25 g of 3-(6,11-dihydro-11-oxodibenz[b,e]oxepin-2-yl)propanoic acid in 500 ml of dry methylene chloride. The chilled stirring suspension was treated dropwise over several minutes with 11.0 ml of thionyl chloride. The suspension was warmed intermittently on a steam bath until all gas evolution ceased. The resulting solution was then allowed to reflux for 15 minutes and was allowed to stand at room temperature under nitrogen atmosphere overnight. The solution was concentrated in vacuo to an oil. The oil was dissolved in 500 ml of methylene chloride and was treated with another 11.0 ml of thionyl chloride. The solution was allowed to reflux for 3 hours and was again concentrated to an oil in vacuo. The oil still contained a significant amount of crystalline impurity, which was filtered away after triturating with a hexane/ether solution. The supernatant was concentrated to an oil in vacuo which solidified overnight in refrigeration. The purified solids were recrystallized from three portions of cyclohexane to give 25.03 g of 3-(6,11-dihydro-11-oxodibenz[b,e]oxepin-2-yl) propanyl chloride, m.p. 69–72° C.

Analysis: Calculated for $C_{17}H_{13}ClO_3$: 67.89%C 4.36%H; Found: 68.05%C 4.61%H

EXAMPLE 13

3-(6,11-Dihydro-11-oxodibenz[b,e]oxepin-2-yl)-N-hydroxy-N-(1-methylethyl)propanamide A stirring solution of 11.58 g of N-isopropylhydroxylamine hydrochloride in 300 ml of dry pyridine was chilled, degassed using several vacuum/$N_2$cycles, and treated dropwise over several minutes with a solution of 7.54 g of 3-(6,11-dihydro-11-oxodibenz[b,e] oxepin-2-yl)propanyl chloride in 200 ml of dry tetrahydrofuran. The solution was allowed to equilibrate to room temperature overnight. The reaction was quenched with 200 ml of water, concentrated in vacuo to remove solvents, and partitioned against a total of 300 ml of methylene chloride and 400 ml of 10% hydrochloric acid (pH of the resulting aqueous phase was below 1). The organic phase was washed with 500 ml of water, dried ($Na_2SO_4$), and concentrated to an oil in vacuo. Thin layer analysis indicated a mixture that was separated via HPLC to give 3.78 g of an oil, which crystallized upon standing at room temperature. The purified solids were recrystallized from acetone/cyclohexane to give 2.50 g of 3-(6,11-dihydro-1-oxo-dibenz[b,e]oxepin-2-yl)-N-hydroxy-N-(1-methylethyl) propanamide, m.p. 117.5–118° C.

Analysis: Calculated for $C_{20}H_{21}NO_4$: 70.78%C 6.24%H 4.13%N; Found: 70.97%C 6.30%H 4.14%N

EXAMPLE 14

3-(6,11-Dihydro-11-oxodibenz[b,e]oxepin-2-yl)-N-ethyl-N-hydroxypropanamide

A stirring solution of 8.98 g of N-ethylhydroxylamine hydrochloride in 300 ml of dry pyridine was chilled, degassed using several vacuum/$N_2$ cycles, and treated dropwise over several minutes with a solution of 9.00 g of 3-(6,11-dihydro-11-oxodibenz[b,e]oxepin-2-yl)propanyl chloride in 200 ml of dry tetrahydrofuran. The solution was allowed to equilibrate to room temperature overnight. The reaction was quenched with 200 ml of water, concentrated in vacuo to remove solvents, and partitioned against a total of 250 ml of methylene chloride and 600 ml of 10% hydrochloric acid (pH of the resulting aqueous phase was below 1). The organic phase was washed with 500 ml of water, dried ($Na_2SO_4$), and concentrated to an oil in vacuo. The oil was triturated with 25% hexane/ethyl acetate to give 6.11 g of solids, which were recrystallized from hexane/ethyl acetate to give 4.56 g of 3-(6,11-dihydro-11-oxodibenz[b,e] oxepin-2-yl)-N-ethyl-N-hydroxypropanamide, m.p. 120° C.

Analysis: Calculated for $C_{19}H_{19}NO_4$: 70.14%C 5.89%H 4.30%N; Found: 69.97%C 5.85%H 4.27%N

EXAMPLE 15

3-(6,11-Dihydro-11-oxodibenz[b,e]oxepin-2-yl)-N-cyclohexyl-N-hydroxypropanamide A stirring solution of 20.5 g of N-cyclohexylhydroxylamine hydrochloride in 300 ml of dry pyridine was chilled, degassed using several vacuum/$N_2$ cycles and was treated dropwise over several minutes with a degassed solution of 13.50 g of 3-(6,11-dihydro-11-oxodibenz[b,e]oxepin-2-yl)propanyl chloride in 300 ml of dry tetrahydrofuran. The resulting solution was allowed to equilibrate to room temperature overnight. The reaction was quenched with 200 ml of water, stirred for an additional 15 minutes, and was concentrated in vacuo to remove solvents. The resulting suspension was partitioned against a total of 300 ml of methylene chloride and 300 ml of 10% hydrochloric acid (pH of the resulting aqueous phase was below 1). The organic phase was washed with 500 ml of water, dried ($Na_2SO_4$), and concentrated to an oil in vacuo. The oil was triturated to an amorphous solid with 25% hexane/ethyl acetate to give 5.26 g of 3-(6,11-dihydro-11-oxodibenz[b,e]oxepin-2-yl)-N-cyclohexyl-N- hydroxypropanamide, m.p. 146–147° C.

Analysis: Calculated for $C_{23}H_{25}NO_4$: 72,80%C 6.64%H 3.69%N; Found: 72.77%C 6.65%H 3.69%N

EXAMPLE 16

2-[[4-(3-Hydroxypropyl)phenoxy]methyl]benzoic acid

A stirring solution of 127.1 g of potassium hydroxide in 500 ml of 95% ethanol was treated portionwise over several minutes with 59.4 g of 2-[[4-(3-hydroxypropyl)phenoxy]methyl]benzoic acid methyl ester. The resulting solution was allowed to reflux overnight with continued stirring. The product solution was poured into 900 ml of water and the solution was acidified to below pH 2 with approximately 200 ml of concentrated hydrochloric acid. The resulting suspension was transferred to a separatory funnel and was partitioned against a total of 1000 ml of ethyl acetate. The primary aqueous phase was discarded and the organic phase was washed with several 500 ml aliquots of water until the pH of the final aqueous phase was neutral. The dried ($Na_2SO_4$) organic phase was concentrated in vacuo to a solid which was recrystallized from ethanol/water to give 49.13 g of 2-[[4-(3-hydroxypropyl)phenoxy]methyl]benzoic acid, m.p. 139–140° C.

Analysis: Calculated for $C_{17}H_{18}O_4$: 71.31%C 6.34%H; Found: 71.42%C 6.27%H

EXAMPLE 17

2-[[4-(3-Hydroxyprolyl)phenoxy]methyl]benzoic acid methyl ester

A stirring degassed suspension of 57.9 g of 3-(4-hydroxyphenyl)propanol, 157 g of potassium carbonate, and a catalytic amount of potassium iodide in 500 ml of 2-butanone was treated dropwise over several minutes with a solution of 87.6 g of 2-(bromomethyl)benzoic acid methyl ester in 500 ml of 2-butanone. The resulting mixture was allowed to reflux for 24 hours and the resulting suspension was then stirred at room temperature for an additional 6 hours. The solids were removed by filtration and the product solution was concentrated to an oil in vacuo. The oil was partitioned against a total of 500 ml of methylene chloride and 1500 ml of 10% aqueous sodium hydroxide. The resulting pH of the final aqueous phase was above 12. The organic phase was washed with 500 ml of water, dried ($Na_2SO_4$), and concentrated to an oil in vacuo. Thin layer analysis indicated a mixture which was separated via HPLC. Poor initial separation gave a mixture, which was separated using hexane in ethyl acetate as eluent to give 68.71 g of 2-[[4-(3-hydroxypropyl)phenoxy]methyl]benzoic acid methyl ester as an oil, which solidified to an amorphous material upon standing at room temperature, m.p. 50.5–52° C.

Analysis:

Calculated for $C_{18}H_{20}O_4$: 71.98%C 6.71%H; Found: 72.04%C 6.61%H

EXAMPLE 18

3-(6,11-Dihydro-11-oxodibenz[b,e]oxepin-2-yl) propyl trifluoroacetate

A stirring suspension of 46.71 g of 2-[[4-(3-hydroxypropyl)phenoxy]methyl]benzoic acid in 500 ml of dry methylene chloride was treated dropwise over several minutes with 82.70 g of trifluoroacetic acid anhydride. The resulting solution was allowed to reflux for 4 hours and was then cooled to ambient temperature and treated with 200 ml of water. The biphasic mixture was acidified with 200 ml of 10% aqueous hydrochloric acid, transferred to a separatory funnel, and the aqueous phase was discarded. The organic phase was partitioned against two 200 ml aliquots of 5% aqueous sodium bicarbonate until the pH of the final aqueous phase was above 8. The organic phase was washed with 500 ml of water, dried ($Na_2SO_4$), and concentrated in vacuo to an oil which solidified upon standing a room temperature. A 5.5 g aliquot of this material was recrystallized from 2,2,4-trimethylpentane (i-octane) to give 3-(6,11-dihydro-11-oxo-dibenz[b,e]oxepin-2-yl)propyl trifluoroacetate, m.p. 40.5–41.0° C.

Analysis: Calculated for $C_{19}H_{15}F_3O_4$: 62.64%C 4.15%H; Found: 62.84%C 4.18%H

EXAMPLE 19

3-(6,11-Dihydro-11-oxodibenz[b,e]oxepin-2-yl) propanol

A stirring degassed solution of 54.03 g of 3-(6,11-dihydro-11-oxodibenz-[b,e]oxepin-2-yl)propyl trifluoroacetate in 300 ml of acetone was treated over several minutes with 250 ml of 10% aqueous hydrochloric acid. The resulting solution was allowed to reflux for 24 hours, cooled to room temperature, and was then concentrated in vacuo to remove acetone. The biphasic mixture was partitioned against a total of 1000 ml of methylene chloride and 1500 ml of 5% aqueous sodium bicarbonate until the pH of the final aqueous phase was above 8. The organic phase was washed with 500 ml of water, dried ($Na_2SO_4$), and concentrated in vacuo to an oil. Thin layer analysis indicated a mixture, which was separated via HPLC (silica gel, eluted with 50% ethyl acetate in hexane) to give 35.77 g of pure 3-(6,11-dihydro-11-oxodibenz[b,e]oxepin-2-yl)propanol, as an oil.

Analysis: Calculated for $C_{17}H_{16}O_3$: 76.10%C 6.01%H; Found: 76.17%C 6.13%H

EXAMPLE 20

3-(6,11-Dihydro-11-oxodibenz[b,e]oxepin-2-yl)-N-hydroxy-N-methyl-1-propylamine A degassed stirring solution of 32.0 g of 3-(6,11-dihydro-11-oxodibenz[b,e]oxepin-2-yl)propanol in 500 ml of sieve dried pyridine was treated dropwise at 0° C. over several minutes with 41.27 g of methanesulfonyl chloride. The resulting solution was allowed to equilibrate to room temperature overnight. The resulting solution was partitioned against a total of 1300 ml of methylene chloride and 2750 ml of 10% aqueous hydrochloric acid. The pH of the final aqueous phase was below 1. The organic phase was washed with 950 ml of water and was dried with 950 ml of saturated aqueous sodium chloride solution. The dried ($Na_2SO_4$) organic phase was filtered over $MgSO_4$ and concentrated in vacuo to a viscous oil. The total yield of pure product was 26.03 g of 3-(6,11-dihydro-11-oxodibenz[b,e]oxepin-2-yl) propanol methanesulfonate.

To a stirring solution of 13.06 g of N-methylhydroxylamine hydrochloride in 250 ml of absolute ethanol was added 17.48 g of potassium tert-butoxide. To the resulting suspension was added 9.0 g of 3-(6,11-dihydro-11-oxodibenz[b,e]oxepin-2 -yl)propanol methanesulfonate. The resulting product suspension was allowed to reflux for 24 hours and was then cooled to room temperature. The suspension was filtered to remove potassium chloride, and the mother liquor was then treated with 200 ml of water and concentrated in vacuo to remove ethanol. The resulting mixture was partitioned against a total of 450 ml of methylene chloride and 250 ml of water. The organic phase was washed with 250 ml of saturated sodium chloride solution, dried ($Na_2SO_4$), filtered, and concentrated in vacuo to a viscous oil which solidified upon triturating the oil, with 10 ml of ethyl acetate and 3 drops of hexane and refrigerating. Thin layer analysis of the solids indicated a mixture, which was separated via HPLC (silica gel). The purified oil solidified upon standing to give 4.03 g of 3-(6,11-dihydro-11-oxodibenz[b,e]oxepin-2-yl)-N-hydroxy-N-methyl-1-propylamine, m.p. 113–114.5° C.

Analysis: Calculated for $C_{18}H_{19}NO_3$: 72.71%C 6.44%H 4.71%N; Found: 72.67%C 6.36%H 4.70%N

EXAMPLE 21

4-(4,10-Dihydro-10-oxothieno[3,2-c][1]benzoxepin-8-yl)butanol methanesulfonate

A chilled stirring solution of 9.5 g of 4-(4,10-dihydro-10-oxothieno[3,2-c][1]benzoxepin-8-yl)butanol in 200 ml of sieve dried pyridine was treated dropwise with 3.80 g of methanesulfonyl chloride and the addition funnel was rinsed with a few ml of methylene chloride. The stirring solution was allowed to equilibrate to room temperature overnight with the bath in place. The resulting solution was poured into 750 ml of water and was allowed to stand for 15 min. The solids were collected by filtration, and dried in vacuo overnight at 42° C. Concentration of the mother liquor produced additional solids which were combined with the first crop and dried to give a total of 9.09 g of crude material. A 2.0 g portion of the product was recrystallized from hexane/ethyl acetate to give 1.3 g of 4-(4,10-dihydro-10-oxothieno[3,2-c][1]benzoxepin-8-yl)butanol methanesulfonate, m.p. 97–98° C.

Analysis: Calculated for $C_{17}H_{18}O_5S_2$: 55.72%C 4.95%H 17.50%S; Found: 56.28%C 5.03%H 17.12%S

EXAMPLE 22

4-(4,10-Dihydro-10-oxothieno[3,2-c][1]benzoxepin-8-yl)-N-hydroxy-N-methyl-1-butylamine To a stirring solution of 4.77 g of N-methylhydroxylamine hydrochloride in 100 ml of absolute ethanol was added 6.38 g of potassium tert-butoxide. To the resulting suspension was added 6.98 g of 4-(4,10-dihydro-10-oxothieno[3,2-c][1]benzoxepin-8-yl)butanol methanesulfonate, and an additional 150 ml of absolute ethanol. The suspension was allowed to reflux for 24 hours and was then cooled to room temperature. The suspension was filtered to remove potassium chloride and the filter cake was washed with absolute ethanol. The resulting solution was concentrated in vacuo to a waxy solid. The solid was dissolved in 300 ml of methylene chloride and partitioned against 200 ml of water. The organic phase was dried with 200 ml of saturated aqueous sodium chloride, collected, dried again ($Na_2SO_4$), filtered, and concentrated in vacuo to an oil. The oil solidified upon standing, and was recrystallized from isopropanol to give 3.09 g of 4-(4,10-dihydro-10-oxothieno[3,2-c][1]benzoxepin-8-yl)-N-hydroxy-N-methyl-1-butylamine, m.p. 107–108° C.

Analysis: Calculated for $C_{17}H_{19}NO_3S$: 64.33%C 6.03%H 4.41%N; Found: 64.31%C 6.04%H 4.30%N

EXAMPLE 23

2-(6,11-dihydro-11-oxodibenz[b,e]oxepin-2-yl)acetaldoxime

A solution of 2-(6,11-dihydro-11-oxodibenz[b,e]oxepin-2-yl)acetyl chloride (15.00 g) in 150 ml of dry diglyme was stirred at –78° C. under nitrogen as lithium tri-tert-butoxyaluminohydride (104.6 ml of a 0.5M solution in diglyme) was added slowly dropwise over one hour. The reaction was stirred ten minutes at –78° C. and then quenched with 3 ml of glacial acetic acid added slowly dropwise. After warming the reaction to room temperature 50 ml of pyridine and 2 equiv. of hydroxylamine hydrochloride (7.27 g) was added and the slurry stirred at 50° C. for two hours. The solvent was evaporated using high vacuum and the residue taken up in chloroform and 1N HCl. The layers were separated and the aqueous phase extracted with chloroform. The combined organic phases were dried ($MgSO_4$), filtered, and evaporated. The residue was purified by flash chromatography (silica; 5:2 hex-EtOAc) and recrystallized from ethyl acetate-hexane to give 2-(6,11-dihydro-11-oxodibenz[b,e]oxepin-2-yl)acetaldoxime, as crystals, m.p. 132–134° C.

Analysis: Calculated for $C_{16}H_{13}NO_3$: 71.90%C 4.90%H 5.24%N; Found: 71.75%C 4.64%H 5.20%N

EXAMPLE 24

N-[2-(6,11-dihydro-11-oxodibenz[b,e]oxepin-2-yl)methyl]-N-Acetyloxyacetamide

A solution of 2-(6,11-dihydro-11-oxodibenz[b,e]oxepin-2-yl)-N-hydroxymethylamine (5.85 g), triethylamine (6.96 g) and 100 ml of dry dichloromethane was stirred at 0° C. under nitrogen as acetyl chloride (3.96 g) was added dropwise. The reaction was stirred at 0° C. for one hour and then poured over 100 ml of 2N HCl. The layers were separated and the aqueous phase extracted with dichloromethane. The combined organic phases were dried ($Na_2SO_4$), filtered, and evaporated. The residue was purified by flash chromatography (silica; 2:1 hex-EtOAc) and recrystallized from ether-hexane to give N-[2-(6,11-dihydro-11-oxodibenz[b,e] oxepin-2-yl)methyl]-N-acetyloxyacetamide, as crystals, m.p. 107–1090° C.

Analysis. Calculated for $C_{19}H_{17}NO_5$: 67.25%C 5.05%H 4.13%N; Found: 67.12%C 4.88%H 4.09%N

EXAMPLE 25

N-[2-(6,11-Dihydro-11-oxodibenz[b,e]oxepin-2-yl)methyl]-N-hydroxyacetamide

A solution of N-[2-(6,11-dihydro-11-oxodibenz[b,e]oxepin-2-yl)methyl]-N-acetyloxyacetamide (2.40 g) in 120 ml of isopropanol was stirred at ambient temperature while 7.0 equiv. of lithium hydroxide monohydrate (2.08 g) in 50 ml of water was added. The reaction was stirred one hour and the isopropanol was evaporated. The residue was partitioned between 2N HCl and ether. The layers were separated and the aqueous phase extracted with additional ether. The combined organic layers were dried ($Na_2SO_4$), filtered, and evaporated. The residue was purified by flash chromatography (silica; 2:1 ethyl acetate-hexane) and recrystallized from ethyl acetate-hexane to give 1.1 g of N-[2-(6,11-dihydro-11-oxodibenz[b,e]oxepin-2-yl)methyl]-N-hydroxyacetamide, m.p. 129–130° C.

Analysis: Calculated for $C_{17}H_{15}NO_4$: 68.68%C 5.09%H 4.71%N; Found: 68.56%C 5.16%H 4.64%N

EXAMPLE 26

N-[2-(6,11-Dihydro-11-oxodibenz[b,e]oxepin-2-yl)ethyl]-N-phenylmethoxy-1,1-dimethylethylcarbamate A solution of tert-butyl N-benzyloxycarbamate (26.8 g) in 100 ml dry dimethylformamide (DMF) was added to a stirred slurry of washed sodium hydride (3.16 g) in 50 ml DMF over 30 minutes. To the resultant solution was added a solution of 2-(6,11-dihydro-11-oxodibenz[b,e]oxepin-2-yl)ethanol methanesulfonate (40 g) in 150 mL dry DMF and the whole stirred at 100° C. overnight. After quenching with water, the biphase was extracted into ethyl acetate, dried, and evaporated. The resulting oil was purified by HPLC (silica gel, 2:1 hexane-ethyl acetate) to give 30 g of N-[2-(6,11-dihydro-11-oxodibenz[b,e]oxepin-2-yl)-ethyl]-N-phenylmethoxy- 1,1dimethylethylcarbamate as an oil.

EXAMPLE 27

N-[2-(6,11-Dihydro-11-oxodibenz[b,e]oxepin-2-yl)ethyl]-N-hydroxy-1,1-dimethylethylcarbamate N-[2-(6,11-dihydro-11-oxodibenz[b,e]oxepin-2-yl-ethyl]-N-hydroxybenzyl-1,1-dimethylethylcarbamate (4.0 g) in 50 ml absolute ethanol was treated with ammonium formate (3.2 g) and 500 mg palladium on carbon. The mixture was stirred at room temperature for 6 hours then filtered through a short pad of celite. The filtrate was evaporated and the residue purified by flash chromatography (silica gel, 7:3 hexane-ethyl acetate) to give an oil. This oil crystallized from hexane-ethyl acetate to give 1.4 g of N-[2-(6,11-dihydro-11-oxodibenz[b,e]oxepin-2-yl)ethyl]-N-hydroxy-1,1-dimethylethylcarbamate, as crystals, m.p. 117–119° C.

Analysis: Calculated for $C_{21}H_{23}NO_5$: 68.28%C 6.28%H 3.79%N; Found: 68.21%C 6.28%H 3.81%N

EXAMPLE 28

2-(6,11-Dihydro-11-oxodibenz[b,e]oxepin-2-yl-N-(phenylmethoxy)ethylamine hydrochloride N-[2-(6,11-dihydro-11-oxodibenz[b,e]oxepin-2-yl)-ethyl]-N-phenylmethoxy-1,1dimethylethylcarbamate (26.0 g) in 200 ml dry ethyl acetate was treated with 90 ml HCl saturated ether and stirred at room temperature for 10 min. The resulting powder was collected and air dried to give 10.58 g of 2-(6,11-dihydro-11-oxodibenz[b,e]oxepin-2-yl)-N-(phenylmethoxy)hydrochloride as a powder.

EXAMPLE 29

N-[2-(6,11-Dihydro-11-oxodibenz[b,e]oxepin-2-yl)ethyl]-N-(phenylmethoxy)acetamide 2-(6,11-Dihydro-11-oxodibenz[b,e]oxepin-2-yl)ethylamine hydrochloride (10.58 g) in 150 ml dry THF was treated with triethylamine (5.3 g) followed by a solution of acetyl chloride (2.38 g) in 20 ml dry THF with stirring. After 2 hours the slurry was filtered and the filtrate evaporated and purified by flash chromatography (silica gel, 2:1 hexane-ethyl acetate) to give 4.07 g of N-[2-(6,11-dihydro-11-oxodibenz[b,e]oxepin-2-yl)ethyl]-N-(phenylmethoxy)acetamide as a semisolid.

EXAMPLE 30

N-[2-(6,11-Dihydro-11-oxodibenz[b,e]oxepin-2-yl)ethyl]-N-hydroxyacetamide

A solution of N-[2-(6,11-dihydro-11-oxodibenz[b,e]oxepin-2-yl)ethyl]-N-(phenylmethoxy)acetamide (4.07 g) in absolute ethanol was treated with ammonium formate (3.2 g) and 700 mg 5% palladium on carbon. The mixture was stirred at room temperature for 1.5 hours then filtered through a short pad of celite. The filtrate was evaporated and the residue purified by flash chromatography (silica gel, 2:1 ethyl acetate-hexane) to give an oil. This oil crystallized from ethyl acetate-hexane to give 1.3 g of N-[2-(6,11-dihydro-11-oxodibenz[b,e]oxepin-2-yl)ethyl]-N-hydroxyacetamide, as crystals, m.p. 113–115° C.

Analysis: Calculated for $C_{18}H_{17}NO_4$: 69.44%C 5.50%H 4.50%N; Found: 69.53%C 5.52%H 4.51%N

EXAMPLE 31

2-(6,11-Dihydro-11-oxodibenz[b,e]oxepin-2-yl)-N-ethyl-N-(ethoxycarbonyloxy)ethylamine A solution of 2-(6,11-dihydro-11-oxodibenz[b,e]oxepin-2-yl-N-ethyl-N-hydroxyethylamine (2.8 g) in 100 ml dry chloroform and triethylamine (1.0 g) was cooled to –5° C. and treated dropwise with a solution of ethyl chloroformate (1.06 g) in 10 ml of dry chloroform The solution was stirred at –5° C. for 15 minutes then washed with brine, dried over $MgSO_4$, filtered and evaporated to an oil. This oil was purified by flash chromatography (silica gel, chloroform) and then by Chromatotron (6000 micron plate, chloroform) to give 1.2 g 2-(6,11-dihydro-11-oxodibenz[b,e]oxepin-2-yl)-N-ethyl-N-(ethoxycarbonyloxy)ethylamine as an oil.

Analysis: Calculated for $C_{21}H_{23}NO_5$: 68.28%C 6.28%H 3.79%N; Found: 68.21%C 6.18%H 3.59%N

EXAMPLE 32

2-(6,11-Dihydro-11-oxodibenz[b,e]oxepin-2-yl)-N-ethyl-N-(acetoxy)ethylamine A solution of 2-(6,11-dihydro-11-oxobenz[b,e]oxepin-2-yl)-N-ethyl-N-hydroxyethylamine (3.0 g) in 60 ml dry chloroform and triethylamine (1.2 g) was cooled to –5° C. and treated dropwise with a solution of acetyl chloride (0.94 g) in 10 ml of dry chloroform. The solution was stirred at –5° C. for 15 minutes then washed with brine, dried over $MgSO_4$, filtered and evaporated to an oil. This oil was purified by flash chromatography (silica gel, chloroform) to give an oil. This oil was crystallized twice from ether-hexane to give 2.4 g of 2-(6,11-dihydro-11-oxodibenz[b,e]oxepin-2-yl)-N-ethyl-N-(acetoxy)ethylamine, as crystals, m.p. 78–81° C.

Analysis: Calculated for $C_{20}H_{21}NO_4$: 70.78%C 6.24%H 4.13%N; Found: 71.03%C 6.19%H 4.09%N

EXAMPLE 33

2-(6,11-Dihydrodibenz[b,e]oxepin-2-yl)ethanol

A solution of 6,11-dihydro-11-oxodibenz[b,e]oxepin-2-acetic acid (100 g) in 450 ml dry tetrahydrofuran (THF) at −5° C. was treated with a 1M solution of borane-THF complex (373 ml in THF) under a nitrogen blanket. After stirring at ambient temperature for 72 hours, the reaction was quenched with methanol then diluted with water. Evaporation of the organic phase left an oily biphase which was basified with saturated sodium bicarbonate and extracted into dichloromethane. The organic phase was dried and evaporated to an oil which was purified by flash chromatography to give 14 g of 2-(6,11-dihydrodibenz[b,e] oxepin-2-yl)ethanol as an oil.

EXAMPLE 34

2-(6,11-Dihydrodibenz[b,e]oxepin-2-yl)ethanol methanesulfonate 2-(6,11-Dihydrodibenz[b,e]oxepin-2-yl)ethanol (14 g) and triethylamine (6.7 g) in 200 ml of dry dichloromethane was treated with methanesulfonylchloride (5.2 ml) and stirred at room temperature for 2 hours. This solution was evaporated to a paste, taken up in ethyl acetate, washed dried, and evaporated to an oil. Passage through a short pad of silica gel with chloroform as eluent gave 13.5 g of 2-(6,11-dihydrodibenz[b,e]-oxepin-2-yl)ethanol methanesulfonate as an oil.

EXAMPLE 35

2-(6,11-Dihydrodibenz[b,e]oxepin-2-yl)-N-ethyl-N-hydroxyethylamine 2-(6,11-Dihydrodibenz[b,e]oxepin-2-yl)ethanol methanesulfonate (13.5 g) was taken up in 20 ml of absolute ethanol and added to a solution containing ethyl hydroxylamine hydrochloride (11.03 g) and potassium t-butoxide (12.7 g) in 600 ml of absolute ethanol. The mixture was stirred at reflux under a nitrogen blanket for 18 hours then evaporated. The residue was taken up in chloroform and washed with brine, dried, and evaporated. Purification of the residual oil (HPLC, 9:1 DCM-methanol) gave an oil which crystallized from ether-hexane. Recrystallization from ether-cyclohexane gave 1.7 g of 2-(6,11-dihydrodibenz[b,e] oxepin-2-yl)-N-ethyl-N-hydroxyethylamine, as crystals, m.p 102–103° C., with softening at 88° C.

Analysis: Calculated for $C_{18}H_{21}NO_2$: 76.30%C 7.47%H 4.94%N; Found: 76.46%C 7.70%H 4.90%N

EXAMPLE 36

2-(6,11-Dihydro-11-hydroxydibenz[b,e]oxepin-2-yl)-N-ethyl-N-hydroxyethylamine

A solution of 2-(6,11-dihydro-11-oxodibenz[b,e]oxepin-2-yl)-N-ethyl-N-hydroxyethylamine (4.1 g) in 100 ml methanol at 0° C. was treated with sodium borohydride (1.04 g) in two portions and stirred under a nitrogen blanket for 2 hours. The solution was evaporated and taken up in chloroform and washed with saturated bicarbonate. This solution was evaporated again and the residue purified by flash chromatography (silica gel, 19:1 Chloroform-methanol) to give an oil. This oil crystallized from ether to give 2.7 g of 2-(6,11-dihydro-1 1-hydroxydibenz[b,e]oxepin-2-yl)-N-ethyl-N-hydroxyethylamine as crystals, m.p. 116–118° C.

Analysis: Calculated for $C_{18}H_{21}NO_3$: 72.22%C 7.07%H 4.68%N; Found: 72.26%C 7.10%H 4.57%N

EXAMPLE 37

3-(6,11-Dihydro-dibenz[b,e]oxepin-2-yl)propanoic acid

A solution of 3-(6,11-dihydro-11-oxo-dibenz[b,e]oxepin-2-yl)propanoic acid (6.0 g) in 120 ml glacial acetic acid was treated with zinc dust (18.0 g) in portions over 1 minute. This slurry was heated at reflux for 2 hours then filtered while hot through a sintered funnel. The filtrate was evaporated, taken up in ethyl acetate and washed with dilute HCl, then dried and evaporated to a solid. This solid was recrystallized from ethyl acetate to give 4.3 g of crystals, m.p. 181–183° C.

Analysis: Calculated for $C_{17}H_{16}O_3$: 76.10%C 6.01%H; Found: 75.59%C 5.93%H

EXAMPLE 38

3-(6,11-Dihydro-dibenz[b,e]oxepin-2-yl)-N-hydroxy-N-methylpropanamide

A slurry of 3-(6,11-dihydro-dibenz[b,e]oxepin-2-yl) propanoic acid (4.9 g) in 100 ml dry DCM was treated with oxalyl chloride (3.1 ml) at 0° C. After one hour, the solution was evaporated to a semisolid. This intermediate acid chloride was taken up in 60 ml dry THF and added over 15 minutes to a stirred mixture containing N-methylhydroxylamine hydrochloride (2.2 g) and triethylamine (7.3 g) in 100 ml THF and 25 ml $H_2O$. After 90 minutes, the mixture was diluted with ethyl acetate, washed with dilute sodium bicarbonate, water, dilute HCl, dried and evaporated to a solid. This solid was recrystallized from ethyl acetate to give 2.7 g of crystals, m.p. 120–122° C.

Analysis: Calculated for $C_{18}H_{19}NO_3$: 72.71%C 6.44%H 4.71%N; Found: 72.47%C 6.51%H 4.61%N

EXAMPLE 39(a)

3-(4-hydroxyphenyl)-2,2-dimethylpropanoic acid ethyl ester

A slurry containing 24.6 g of zinc dust in 100 ml dry toluene was treated dropwise with a solution containing 73.5 g of ethyl bromoisobutyrate and 65 g of 4-acetoxybenzaldehyde in 200 ml dry toluene. A crystal of iodine was added to initiate the reaction and the mixture was heated to reflux overnight. An additional equivalent of ethyl bromoisobutyrate was added and reflux was continued for 24 hours. After cooling, the filtrate was hydrogenated over palladium and the residue purified by flash chromatography to give 12.2 g of 3-(4-hydroxyphenyl)-2,2-dimethylpropanoic acid ethyl ester as an oil.

EXAMPLE 39(b)

2-[4-(2-ethoxycarbonyl-2-methylpropyl) phenoxymethyl]-benzoic acid ethyl ester 3-(4-hydroxyphenyl)-2,2-dimethylpropanoic acid ethyl ester (12.2 g) was added to a slurry containing 6.46 g of potassium tert-butoxide in 55 ml dry dimethylformamide at 0° C. After 30 minutes, a solution containing 12.6 g of ethyl (α-bromo-ortho-toluate in 15 ml dry dimethylformamide was added and the solution stirred for 2 hours at room temperature, then at 50° C. overnight. Dilution with water, extraction with ether and evaporation left an oil which was purified by HPLC (silica gel, 7:3 dichloromethane-heptane) to give 20.3 g of 2-[4-(2-ethoxycarbonyl-2-methylpropyl) phenoxymethyl]benzoic acid ethyl ester as an oil.

EXAMPLE 39(c)

2-[4-(2-carboxy-2-methylpropyl)phenoxymethyl] benzoic acid

A solution containing 30.2 g of potassium hydroxide in 150 ml 95% ethanol was added to 2-[4-(2-ethoxycarbonyl- 2-methylpropyl)phenoxymethyl]benzoic acid ethyl ester (20.3 g) and warmed to reflux for 8 hours. The solution was cooled, diluted with water and adjusted to pH 5 with 6N HCl. Cooling overnight gave a precipitate which was collected and air dried to give 15.9 g of 2-[4-(2-carboxy-2-methylpropyl)phenoxymethyl]benzoic acid as a powder.

EXAMPLE 39(d)

3-(6,11-dihydro-11-oxodibenz[b,e]oxepin-2-yl)2,2-dimethylpropanoic acid

A slurry of 2-[4-(2-carboxy-2-methylpropyl)phenoxymethyl]benzoic acid (15.9 g) in 200 ml dry dichloromethane was treated dropwise with 12.5 ml trifluoroacetic anhydride then heated to reflux for 5 hours. Evaporation left an oil which was purified by HPLC (20:1 dichloromethane-methanol) to give 2.95 g of 3-(6,11-dihydro-11-oxodibenz[b,e]oxepin-2-yl)-2,2-dimethyl-propanoic acid a solid.

EXAMPLE 39(e)

3-(6,11-Dihydro-11-oxodibenz[b,e]oxepin-2-yl)-2,2-dimethyl-N-hydroxy-N-methyl propanamide A slurry of 3-(6,11-dihydro-11-oxodibenz[b,e]oxepin-2-yl)-2,2-dimethyl-propanoic acid (2.0 g) in 20 ml dry DCE and 0.1% DMF was treated with thionyl chloride (0.9 g) and warmed to 50° C. for 2 hours. Evaporation gave the acid chloride as an oil. A solution of N-methylhydroxylamine hydrochloride (0.9 g) in 30 ml dry DMF at −10° C. was treated with triethylamine (2.1 g) and stirred for 15 minutes. To the resulting slurry was added a solution of the acid chloride in 10 ml dry ethyl acetate. After stirring at room temperature for 2 hours the mixture was diluted with 200 ml H₂O and the product collected. This powder was recrystallized from ethyl acetate-methanol to give 1.2 g of crystals, m.p. 192–194° C.

Analysis Calculated for $C_{20}H_{21}NO_4$: 70.78%C 6.24%H 4.13%N; Found: 70.56%C 6.26%H 4.10%N

We claim:

1. A compound of the formula

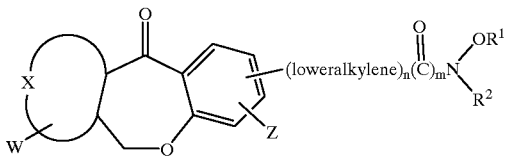

wherein X together with the carbon atoms to which it is attached forms a benzene or thiophene ring W and Z are independently hydrogen, halogen, loweralkyl or trifluoromethyl; $R^1$ is hydrogen, arylloweralkyl, loweralkoxycarbonyl, loweralkylcarbonyl, arylcarbonyl or arylloweralkylcarbonyl; $R^2$ is loweralkyl, cycloalkyl, arylloweralkyl, loweralkoxycarbonyl, loweralkylcarbonyl or arylloweralkylcarbonyl; m is 0 or 1 and n is an integer from 0 to 4; or a pharmaceutically acceptable salt thereof, with the proviso that when X together with the carbon atoms to which it is attached forms a benzene ring, then m is 0, $R^1$ is hydrogen and $R^2$ is loweralkoxycarbonyl, loweralkylcarbonyl, arylcarbonyl or arylloweralkylcarbonyl.

2. The compound as defined in claim 1 wherein X together with the carbon atoms to which it is attached forms a benzene ring.

3. The compound as defined in claim 1 which is N-[2-(6,11-dihydro-11-oxodibenz[b,e]-oxepin-2-yl)methyl]-N-hydroxyacetamide.

4. The compound as defined in claim 1 which is N-[2-(6,11-dihydro-11-oxo-dibenz[b, e]oxepin-2-yl)ethyl]-N-hydroxyacetamide.

5. The compound as defined in claim 1 wherein X together with the carbon atoms to which it is attached forms a thiophene ring.

6. The compound as defined in claim 5 wherein m=0.

7. The compound as defined in claim 6 which is 4-(4,10-dihydro-10-oxothieno[3,2-c][1]benzoxepin-8-yl)-N-hydroxy-N-methyl-1-butylamine.

8. The compound as defined in claim 5 wherein m=1.

9. A compound of the formula

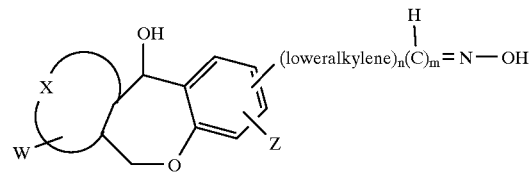

where X together with the carbon atoms to which it is attached forms a benzene or thiophene ring; W and Z are independently hydrogen, halogen, loweralkyl or trifluoromethyl; n is an integer from 0 to 4; or a pharmaceutically acceptable salt thereof.

10. A compound as defined in claim 9 wherein n=1.

11. The compound as defined in claim 10 which is 2-(6,11-dihydro-11-oxodibenz[b,e]-oxepin-2-yl)acetaldoxime.

12. A compound of the formula

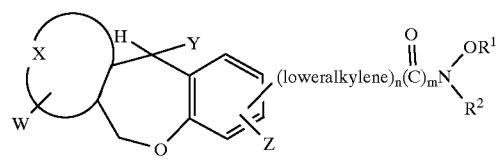

wherein X together with the carbon atoms to which it is attached forms a benzene or thiophene ring; Y is hydrogen or OH; W and Z are independently hydrogen, halogen, loweralkyl or trifluoromethyl; $R^1$ is hydrogen, arylloweralkyl, loweralkoxycarbonyl, loweralkylcarbonyl, arylcarbonyl or arylloweralkylcarbonyl; $R^2$ is loweralkyl, cycloalkyl, arylloweralkyl, loweralkoxycarbonyl, loweralkylcarbonyl, arylcarbonyl or arylloweralkylcarbonyl; m is 0 or 1; n is an integer from 0 to 4; or a pharmaceutically acceptable salt thereof.

13. A compound as defined in claim 12 wherein Y is hydrogen.

14. The compound as defined in claim 13 which is 2-(6,11-dihydrodibenz[b,e]oxepin-2-yl)-N-ethyl-N-hydroxyethylamine.

15. The compound as defined in claim 13 which is 3-(6,11-dihydro-dibenz[b,e]oxepin-2-yl)-N-hydroxy-N-methylpropanamide.

16. A compound as defined in claim 12 wherein Y is OH.

17. The compound as defined in claim 16 which is 2-(6,11-dihydro-11-hydroxy-dibenz[b,e]oxepin-2-yl)-N-ethyl-N-hydroxyethylamine.

18. The compound as defined in claim 2 which is 3-(6,11-dihydro-11-oxodibenz[b,e]-oxepin-2-yl)-2,2-dimethyl-N-hydroxy-N-methyl propanamide.

19. An analgesic composition which comprises an effective pain alleviating amount of a compound as defined in claim 1 and a suitable carrier therefor.

20. An analgesic composition which comprises an effective pain alleviating amount of the compound as defined in claim 9 and a suitable carrier therefor.

21. A pharmaceutical composition for treating a dermatosis which comprises a compound as defined in claim 1 in an amount effective for treating a dermatosis and a suitable carrier therefor.

22. A pharmaceutical composition for treating a dermatosis which comprises a compound as defined in claim 12 in an amount effective for treating a dermatosis and a suitable carrier therefor.

23. A pharmaceutical composition for treating conditions where accumulation of cyclooxygenase and/or lipoxygenase metabolites is a causative factor which comprises a compound as defined in claim 1 in an amount effective for treating conditions where accumulation of cyclooxygenase and/or lipoxygenase metabolites is a causative factor and a suitable carrier therefor.

24. A pharmaceutical composition for treating conditions where accumulation of cyclooxygenase and/or lipoxygenase metabolites is a causative factor which comprises a compound as defined in claim 12 in an amount effective for treating conditions where accumulation of cyclooxygenase and/or lipoxygenase metabolites is a causative factor and a suitable carrier therefor.

25. A method of alleviating pain which comprises administering to a patient a pain alleviating effective amount of a compound as defined in claim 1.

26. A method of alleviating pain which comprises administering to a patient a pain alleviating effective amount of compound as defined in claim 9.

27. A method of treating dermatoses which comprises administering to a patient a dermatoses treating effective amount of a compound as defined in claim 1.

28. A method of treating dermatoses which comprises administering to a patient a dermatoses treating effective amount of a compound as defined in claim 9.

29. A method of treating conditions where accumulation of cyclooxygenase and/or lipoxygenase metabolites is a causative factor which comprises administering to a patient an effective amount to treat said condition of a compound as defined in claim 1.

30. A method of treating conditions where accumulation of cyclooxygenase and/or lipoxygenase metabolites is a causative factor which comprises administering to a patient an effective amount to treat said condition of a compound as defined in claim 9.

* * * * *

UNITED STATES PATENT AND TRADEMARK OFFICE
CERTIFICATE OF CORRECTION

PATENT NO. : 5,917,057

DATED : June 29, 1999

INVENTOR(s) : Richard C. Allen et al.

It is certified that error appears in the above-identified patent and that said Letters Patent is hereby corrected as shown below:

Column 9, formula XXV, that portion of the formula reading $N-O(arylmentyl)$ should read $N-O(arylmethyl)$ Column 9, Line 16 to 17 read: " that so described" and should read --that described--.

Column 9, line 23 reads "(XXV)" and should read --(XXVI)--.

Column 9, formula XXVI, that portion of the formula reading $N-O(arylmentyl)$ should read $N-O(arylmethyl)$ Column 14, Line 55 reads: "strearate" and should read --stearate--.

Column 16, Line 24 reads as "-N-hydroxyacetylacetamide" and should read ---N-acetyloxyacetamide--.

Column 16, Line 30 reads: "N-hydroxy-1,1-dimethylethylcarbamate; mine;" and should read --N-hydroxy-1,1-dimethylethylcarbamate;--.

Column 16, Line 32 reads as "N-acetyloxyacetamide" and should read --N-hydroxyacetamide--.

Column 16, Line 39 reads: "2-Dihydro-11-hydroxy" and should read --2-(6,11-Dihydro-11-hydroxy--.

Column 16, Line 62 reads: "N-phenylmethoxy-phenylmethoxy-1-" and should read --N-phenylmethoxy-1---.

Column 19, Line 55 reads: "1-oxodibenz" and should read --11-oxodibenz--.

Column 20, Line 20 reads: "2-(6,11-dihydro11oxodibenz" and should read --2-(6,11-dihydro-11-oxodibenz--.

Column 20, Line 36 reads: "4.50%N; 20 Found:" and should read --4.50%N; Found:--.

Column 21, Line 25 reads: "hydroxypropana" and should read --hydroxypropanamide--.

UNITED STATES PATENT AND TRADEMARK OFFICE
CERTIFICATE OF CORRECTION

PATENT NO. : 5,917,057

DATED : June 29, 1999

INVENTOR(s) : Richard C. Allen et al.

It is certified that error appears in the above-identified patent and that said Letters Patent is hereby corrected as shown below:

Column 21, Line 46 reads: "mixture a which" and should read --mixture which--.

Column 23, Line 53 reads: "Hydroxyprolyl" and should read --Hydroxypropyl--.

Column 32, claim 9, that portion of the formula reading

Column 32, Claim 19, Line 67 reads: "therefor" and should read --therefore--.

Column 33, Claim 20, Line 3 reads: "therefor" and should read --therefore--.

Column 33, Claim 21, Line 7 reads "therefor" and should read --therefore--.

Column 33, Claim 22, Line 11 reads "therefor" and should read --therefore--.

Column 33, Claim 23, Line 18 reads "therefor" and should read --therefore--.

Column 33, Claim 24, Line 25 reads "therefor" and should read --therefore--.

Signed and Sealed this

Twenty-ninth Day of May, 2001

Attest:

NICHOLAS P. GODICI

*Attesting Officer*   *Acting Director of the United States Patent and Trademark Office*